(12) United States Patent
Hodge et al.

(10) Patent No.: US 7,851,541 B2
(45) Date of Patent: *Dec. 14, 2010

(54) COMPOSITION AND USE

(75) Inventors: David John Hodge, Moreton-on-Lugg (GB); David Alan Pears, Poynton (GB); John Jeffrey Gerrard, Chester (GB); Paula Louise McGeechan, Bury (GB)

(73) Assignee: Arch UK Biocides Limited, Blackley, Manchester (GB)

( * ) Notice: Subject to any disclaimer, the term of this patent is extended or adjusted under 35 U.S.C. 154(b) by 860 days.

This patent is subject to a terminal disclaimer.

(21) Appl. No.: 11/796,510

(22) Filed: Apr. 27, 2007

(65) Prior Publication Data

US 2007/0203285 A1    Aug. 30, 2007

Related U.S. Application Data

(62) Division of application No. 10/850,069, filed on May 20, 2004, now Pat. No. 7,217,759.

(60) Provisional application No. 60/471,736, filed on May 20, 2003.

(51) Int. Cl.
*C08G 81/02* (2006.01)
(52) U.S. Cl. .................. 524/514; 524/457; 524/237; 524/195; 525/293; 525/63
(58) Field of Classification Search ................ 524/514, 524/457, 237, 195; 525/293, 63
See application file for complete search history.

(56) References Cited

U.S. PATENT DOCUMENTS 6,497,868 B1    12/2002    Tanahashi

| | | | |
|---|---|---|---|
| 6,555,225 B1 * | 4/2003 | Yoshioka et al. | ......... 428/411.1 |
| 2001/0007063 A1 | 7/2001 | Oyama et al. | |
| 2002/0035357 A1 | 3/2002 | Faour et al. | |
| 2003/0224030 A1 | 12/2003 | Uchiyama et al. | |

FOREIGN PATENT DOCUMENTS

| EP | 0182523 | | 5/1986 |
|---|---|---|---|
| EP | 0232006 | | 8/1987 |
| EP | 0522668 | | 1/1993 |
| GB | 2213721 | | 8/1989 |
| JP | 61152605 | | 7/1986 |
| JP | 11099200 | * | 4/1999 |
| JP | 11099200 | A | 4/1999 |
| WO | 97/05910 | | 2/1997 |
| WO | 00/02449 | | 1/2000 |
| WO | 00/65915 | | 11/2000 |
| WO | 02/28952 | | 4/2002 |
| WO | WO 02/28952 | * | 4/2002 |

OTHER PUBLICATIONS

"Principals of Polymerisation," G. Odian, Wiley, Interscience, 3$^{rd}$ Ed., 1991, pp. 303-355.

P. Silley, et al., "Impedance Microbiology—A Rapid Change for Microbiologists," Journal of Applied Biotechnology, vol. 80, 1996, pp. 233-243.

* cited by examiner

*Primary Examiner*—Ling-Siu Choi
(74) *Attorney, Agent, or Firm*—Dale L. Carlson; Wanli Wu; Wiggin and Dana LLP

(57) ABSTRACT

A composition containing an anti-microbial agent that comprises a polymeric biguanide, either alone or in combination with at least one other microbiologically active component. The composition also includes an amphoteric co-polymer of the Formula (1):

(i) group consisting of quaternary ammonium compounds,

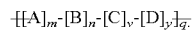

Formula (1)

8 Claims, 9 Drawing Sheets

Polymer Cloud Point Variation as a Function of methyl methacrylate (MMA) Content (Component [A] in Formula 1) in Polymers 19, 20, and 21 which all contain MPEG550MA ■ Polymer 19,  ▲ Polymer 20,  ● Polymer 21

Polymer Cloud Point Variation as a Function of methyl methacrylate (MMA) Content (Component [A] in Formula 1) in Polymers 10, 11 and 12, all of which contain MPEG350MA.

■ Polymer 10,   ▲ Polymer 11,   ● Polymer 12

UV Spectroscopic Calibration Curve for Poly(hexamethylene biguanide) (PHMB) concentation measured at 236 nm ■ PHMB only  ◆ Composition 22 (Co-polymer 5: PHMB , 95:5 w/w%)

Release of PHMB from Coatings of Amphoteric co-polymer/PHMB Compositions 1, 8 and 22 (Table 2).

◆ Composition 1, ■ Composition 8, ▲ Composition 22

Release of PHMB from Coatings of Amphoteric co-polymer/PHMB Compositions 8, 44 and 61 (Table 2) at 5% PHMB concentration.

◆ Composition 61, ■ Composition 44, ▲ Composition 8

Release of PHMB from Coatings of Amphoteric co-polymer/PHMB Compositions 22 and 25 (Table 2) at 5% PHMB concentration.

■ Composition 25    ▲ Composition 22

Release of PHMB from Coatings of Amphoteric co-polymer/PHMB Compositions 8 and 3 (Table 2)

• Composition 8   ▲ Composition 3

Release of PHMB from Coatings of Amphoteric co-polymer/PHMB Compositions 25, 91 and 93 (Table 2).

◆ Composition 91   ■ Composition 93   ▲ Composition 25

Release of PHMB from Coatings of Amphoteric Co-polymer/PHMB Compositions 8, 44 and 50 (Table 2)

♦ Composition 8    ■ Composition 44    ▲ Composition 50

COMPOSITION AND USE

CROSS-REFERENCE TO RELATED CASES

This is a divisional application of U.S. Ser. No. 10/850,069, filed on May 20, 2004, which claims priority to U.S. Provisional Patent Application No. 60/471,736, filed May 20, 2003, entitled "COMPOSITION AND USE", by David John Hodge et al. now U.S. Pat. No. 7,217,759. The disclosure of both U.S. Ser. No. 10/850,069 and U.S. Ser. No. 60/471,736 are incorporated by reference herein in their entireties.

BACKGROUND OF THE INVENTION

1. Field of the Invention

The present invention relates to a method for inhibiting the growth of micro-organisms on surfaces by means of a composition comprising an amphoteric vinyl comb type co-polymer and an antimicrobial agent. The antimicrobial agent is controllably released from the amphoteric co-polymer over time thereby providing effective anti-microbial control.

Micro-organisms can be found on many inanimate and animate surfaces. The presence of such micro-organisms can result in unhygienic conditions in hospitals and medical environments, kitchens, bathrooms, toilets and in the preparation and packaging of foodstuffs leading to health risks and contamination.

Several anti-microbial agents exist which are effective against many of the virulent forms of micro-organisms found in the food and health-care environments. Unfortunately, the activity of such agents is insufficient in terms of providing a sustained, surface hygienic effect. This may be due to the high water solubility and/or lack of substantivity of the anti-microbial agent on a surface which means that the anti-microbial agent is readily displaced. There is therefore a requirement for an anti-microbial agent or an anti-microbial agent in combination with a delivery system which provides a high degree of anti-microbial kill over a sustained period of time.

2. Brief Description of Art

The literature describes various cases where micro-organisms and in particular bacterial fouling may cause damage or lead to contamination of surfaces including for example swimming pools, industrial pipes, architectural structures, ships hulls, hospital theatres, teeth and kitchen surfaces. Indeed, there have been many attempts and approaches to overcome the micro-biological problems associated especially with bacterial growth on inanimate and animate surfaces.

European Patent 0182523 describes how certain polymeric compositions are effective at preventing oral bacteria from colonisation on the surface of teeth. In UK Patent 2213721, an anti-staining composition comprising polymers with anti-bacterial agents were shown to be effective against bacteria found in an oral environment.

In European Patent 0232006, coating compositions comprising sulphonated polymers and a microbicide for use in marine environments were shown to have hydrolytic instability. In the above cases the coating of a polymer in an aqueous environment with or without microbicide was substantially erodable, thereby acting by means of a self-polishing effect, thereby reducing the ability of bacteria to colonise on the surface to be protected.

WO/02449 describes a process for the biocidal treatment of surfaces comprising high molecular weight grafted co-polymers.

However, none of the above documents describe an anti-microbial system which has both the ability to eliminate micro-organisms effectively and has a sustained, surface hygienic effect.

The term 'sustained' used hereinafter refers to an anti-microbial agent which is still active even after the surface to which the agent has been applied has been cleansed for example by wiping, rinsing or washing the surface.

BRIEF DESCRIPTION OF THE DRAWINGS

The invention will be more fully understood from the following detailed description taken in conjunction with the accompanying drawings in which.

DESCRIPTION OF THE INVENTION

Figure 1:
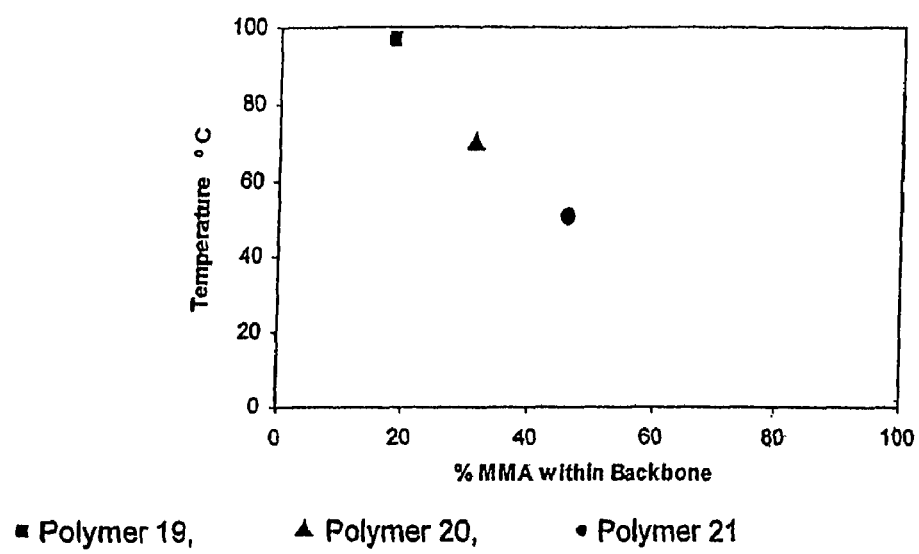
FIG. 1 shows a graph of the polymer cloud point variation as a function of methyl methacrylate in polymers 19, 20 and 21.

Surprisingly, we have now found that a combination of certain anti-microbial agents and amphoteric vinyl comb type co-polymers (referred to hereinafter as amphoteric co-polymers) provides effective and sustained anti-microbial activity when used to inhibit the growth of micro-organisms on surfaces. The present invention therefore provides compositions for the treatment of surfaces based on amphoteric co-polymers with varying functionality in both the backbone and the side chain in combination with an anti-microbial agent, especially a biocide.

Consequently, according to a first aspect of the present invention there is provided a composition comprising:

(i) an anti-microbial agent comprising a polymeric biguanide, alone or in combination with at least one other microbiologically active component selected from the group consisting of quaternary ammonium compounds, monoquaternary heterocyclic amine salts, urea derivatives, amino compounds, imidazole derivatives, nitrile compounds, tin compounds or complexes, isothiazolin-3-ones, thiazole derivatives, nitro compounds, iodine compounds, aldehyde release agents, thiones, triazine derivatives, oxazolidine and derivatives thereof, furan and derivatives thereof, carboxylic acids and the salts and esters thereof, phenol and derivatives thereof, sulphone derivatives, imides, thioamides, 2-mercapto-pyridine-N-oxide, azole fungicides, strobilurins, amides, carbamates, pyridine derivatives, compounds with active halogen groups, and organometallic compounds; and (ii) an amphoteric co-polymer of the Formula (1):

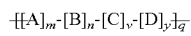  Formula (1)

wherein

[A] is of Formula (9),

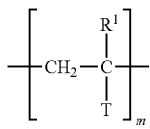 Formula (9)

[B] is of Formula (10),

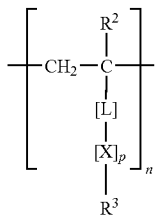 Formula (10)

[C] is of Formula (12),

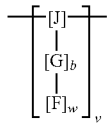 Formula (12)

[D] is of Formula (13),

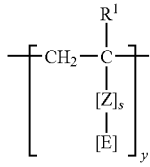 Formula (13)

and X is of Formula (11),

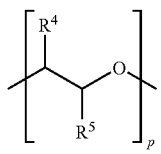 Formula (11)

wherein [A], [B] and [D] may occur in any order;
T is an optionally substituted substitutent;
L, G and Z each independently is an optionally substituted linking group;
$R^1$, $R^2$ and $R^3$ are each independently H, optionally substituted $C_{1-20}$-alkyl or optionally substituted $C_{3-20}$-cycloalkyl;
$R^4$ and $R^5$ are each independently H or $C_{1-4}$-alkyl;
q is 15 to 1000;
p is 3 to 50;
J is an optionally substituted hydrocarbyl group;
F is an acidic substitutent;
E is a basic substitutent;
m is 0 to 350;
n is 1 to 75;
v is 0 to 100;
y is 1 to 100;
b is 0, 1 or 2;
s is 0 or 1;
w is 1 to 4; and
provided that at least one of $R^4$ and $R^5$ is H.

A preferred anti-microbial agent for use in the composition according to the first aspect of the present invention is an anti-bacterial agent, more preferably a polymeric biguanide.

Polymeric Biguanide

Preferably the polymeric biguanide comprises at least two biguanide units of Formula (2):

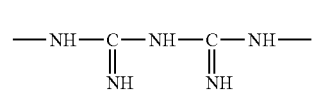 Formula (2)

linked by a bridging group which contains at least one methylene group. The bridging group preferably includes a polymethylene chain, optionally incorporating or substituted by one or more hetero atoms such as oxygen, sulphur or nitrogen. The bridging group may include one or more cyclic moieties which may be saturated or unsaturated. Preferably, the bridging group is such that there are at least three, and especially at least four, carbon atoms directly interposed between two adjacent biguanide units of Formula (2). Preferably, there are not greater than ten and especially not greater than eight carbon atoms interposed between two adjacent biguanide units of Formula (2).

The polymeric biguanide may be terminated by any suitable group, such as a hydrocarbyl, substituted hydrocarbyl or an amine group or a cyanoguanidine group of the Formula (3):

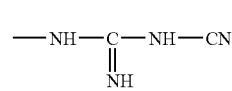 Formula (3)

When the terminating group is hydrocarbyl, it is preferably alkyl, cycloalkyl, aryl or aralkyl. When the hydrocarbyl group is alkyl it may be linear or branched but is preferably linear.

Preferred alkyl groups include $C_{1-8}$-alkyl. Examples of preferred alkyl groups include for example methyl, ethyl, n-propyl, isopropyl, n-pentyl, n-butyl, isobutyl, tert-butyl and n-octyl.

When the hydrocarbyl group is cycloalkyl, it is preferably cyclopropyl, cyclopentyl or cyclohexyl. When the hydrocarbyl group is aralkyl, it preferably contains from 1 to 6, more preferably 1 or 2 carbon atoms in the alkylene group attaching the aryl group to the biguanide. Preferred aralkyl groups include benzyl and 2-phenylethyl groups.

Preferred aryl groups include phenyl groups. When the terminating group is substituted hydrocarbyl, the substitutent may be any substitutent that does not exhibit undesirable adverse effects on the microbiological properties of the polymeric biguanide. Examples of such substitutents are aryloxy, alkoxy, acyl, acyloxy, halogen and nitrile.

When the polymeric biguanide contains two biguanide groups of Formula (2) the biguanide is a bisbiguanide. The two biguanide groups are preferably linked through a polymethylene group, especially a hexamethylene group.

The polymeric biguanide preferably contains more than two biguanide units of Formula (2) and is preferably a linear polymeric biguanide which has a recurring polymeric chain represented by Formula (4) or a salt thereof:

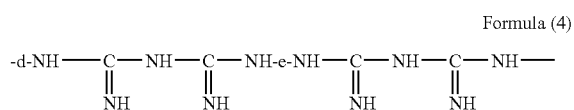

Formula (4)

wherein d and e represent bridging groups which may be the same or different and in which together the total of the number of carbon atoms directly interposed between the pairs of nitrogen atoms linked by d plus the number of carbon atoms directly interposed between the pairs of nitrogen atoms linked by e is more than 9 and less than 17.

The bridging groups d and e preferably consist of polymethylene chains, optionally interrupted by hetero atoms, for example, oxygen, sulphur or nitrogen. d and e may also incorporate moieties which may be saturated or unsaturated, in which case the number of carbon atoms directly interposed between the pairs of nitrogen atoms linked by d and e is taken as including that segment of the cyclic group, or groups, which is the shortest. Thus, the number of carbon atoms directly interposed between the nitrogen atoms in the group

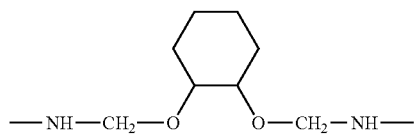

is 4 and not 8.

The linear polymeric biguanides having a recurring polymer unit of Formula (4) are typically obtained as mixtures of polymers in which the polymer chains are of different lengths. Preferably, the number of individual biguanide units of Formulae (5a) and (5b):

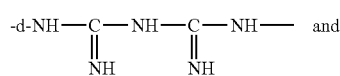
Formula (5a)

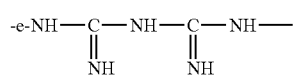
Formula (5b)

is, together, from 3 to about 80.

The preferred linear polymeric biguanide is a mixture of polymer chains in which d and e are identical and the individual polymer chains, excluding the terminating groups, are of the Formula (6) or a salt thereof:

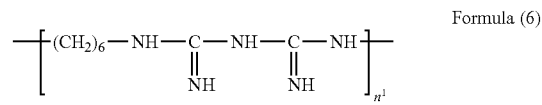

Formula (6)

wherein $n^1$ is from 4 to 20 and especially from 4 to 18. It is especially preferred that the average value of $n^1$ is about 16. Preferably, the average molecular weight of the polymer in the free base form is from 1100 to 4000.

The linear polymeric biguanides may be prepared by the reaction of a bisdicyandiamide having the Formula (7):

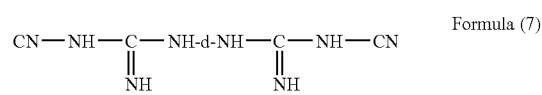

Formula (7)

with a diamine $H_2N$-e-$NH_2$, wherein d and e have the meanings defined above, or, by the reaction between a diamine salt of dicyanamide having the Formula (8):

Formula (8)

with a diamine $H_2N$-e-$NH_2$ wherein d and e have the meanings defined above. These methods of preparation are described in UK specifications numbers 702,268 and 1,152,243 respectively, and any of the polymeric biguanides described therein may be used in the present invention.

As noted hereinbefore, the polymer chains of the linear polymeric biguanides may be terminated either by an amino group or by a cyanoguanidine group of Formula (9):

Formula (9)

This cyanoguanidine group can hydrolyse during preparation of the linear polymeric biguanide yielding a guanidine end group. The terminating groups may be the same or different on each polymer chain.

A small proportion of a primary amine R—$NH_2$, where R represents an alkyl group containing from 1 to 18 carbon atoms, may be included with the diamine $H_2N$-e-$NH_2$ in the preparation of polymeric biguanides as described above. The primary amine acts as a chain-terminating agent and consequently one or both ends of the polymeric biguanide polymer chains may be terminated by an —NHR group. These —NHR chain-terminated polymeric biguanides may also be used.

The polymeric biguanides readily form salts with both inorganic and organic acids. Preferred salts of the polymeric biguanide are water-soluble.

It is especially preferred that the polymeric biguanide used in accordance with the present invention is a mixture of linear polymers, the individual polymer chains of which, excluding the terminating groups, are represented by Formula (6) in the hydrochloride salt form. This poly(hexamethylenebiguanide) compound is commercially available from Avecia Limited under the trademarks Vantocil™, Cosmocil™ and Reputex™.

Amphoteric Co-polymers

Preferably the amphoteric co-polymers of the present invention are as illustrated in the following Empirical Structural Formula.

Empirical Structural Formula

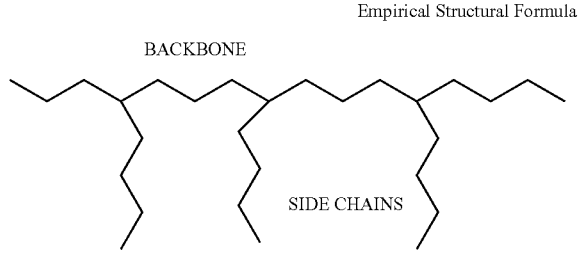

The amphoteric co-polymers comprise at least one polymer which comprises one or more repeating units of the Formula (1) wherein the side chains are introduced via component [B],

   Formula (1)

wherein

[A] is of Formula (9),

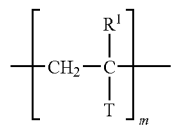   Formula (9)

[B] is of Formula (10),

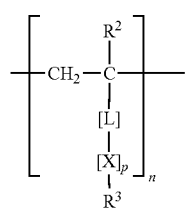   Formula (10)

[C] is of Formula (12),

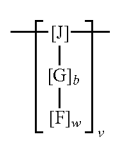   Formula (12)

[D] is of Formula (13),

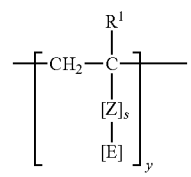   Formula (13)

and X is of Formula (11),

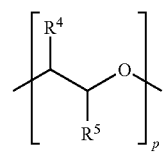   Formula (11)

wherein [A], [B], [C] and [D] may occur in any order;
T is an optionally substituted substitutent;
L, G and Z each independently is an optionally substituted linking group;
$R^1$, $R^2$ and $R^3$ are each independently H, optionally substituted $C_{1-20}$-alkyl or optionally substituted $C_{3-20}$-cycloalkyl;
$R^4$ and $R^5$ are each independently H or $C_{1-4}$-alkyl;
q is 15 to 1000;
p is 3 to 50;
J is an optionally substituted hydrocarbyl group;
F is an acidic substitutent;
E is a basic substitutent;
m is 0 to 350;
n is 1 to 75;
v is 0 to 100;
y is 1 to 100;
b is 0, 1 or 2;
s is 0 or 1; and
w is 1 to 4; and provided that one at least one of $R^4$ and $R^5$ is H.

The term amphoteric means that the polymer contains both positive (cationic or basic species capable of being protonated) and negative (anionic or acidic species capable of forming salts) in the form of [D] and [C] respectively. In acidic solutions the basic units [D] will form cations and the co-polymer will be positively charged overall. In alkaline solutions, the acidic units [C] will form anionic species and the polymer will be negatively charged. As the pH approaches neutral (pH 7) the co-polymer will have both negative and positive charges and is hence termed zwitterionic in nature. Alternatively, the amphoteric co-polymer may be zwitterionic as a result of the incorporation of a zwitterion into [D].

The term quaternised internal salt can also be used to refer to Formula (1), in which case [C] is itself a quaternised internal salt. The term amphoteric co-polymer referred to herein is used to describe a co-polymer which can be derived from an addition polymerisation reaction, that is, a free radical initiated process which can be carried out in either an aqueous or non aqueous medium of three or more olefinically unsaturated monomers. Therefore, the term vinyl monomer used throughout refers to an olefinically unsaturated monomer.

Examples of vinyl monomers which may be used to form the amphoteric co-polymers for use in the present invention include but are not limited to styrene, α-methyl styrene, benzyl methacrylate, acrylonitrile, methacrylonitrile, vinyl polyethers of ethylene or propylene oxide such as hydroxypolyethoxy (5) polypropoxy (5) monoallyl ether (BX-AA-E5P5 available from Bimax Chemicals Ltd), N,N-diethyl amino ethyl(meth)acrylate, N,N-dimethyl amino ethyl(meth)acrylate, N,N-dipropyl amino ethyl(meth)acrylate, N,N-diethyl amino ethyl(meth)acrylamide, N,N-dimethyl amino ethyl (meth)acrylamide, tertiary butyl amino ethyl methacrylate, N,N-dimethyl amino propyl(meth)acrylamide, N,N-dimethyl amino propyl(meth)acrylate, 4-vinyl pyridine, 2-vinyl pyridine, vinyl imidazole, N,N-dimethyl amino methyl styrene, 4-amino styrene, N,N-dimethyl amino styrene, amino methyl styrene. Basic amine bearing monomers may be polymerised as the free amine, as a protonated salt or as a quaternised amine salt, for example, basic quaternary ammonium monomers such as N,N-dimethyl amino ethyl acrylate methyl chloride quaternary salt (available from Ciba Specialty Chemicals as AGEFLEX FA1Q80MC or from Mitsubishi Rayon Co. Ltd as DMCMA), N,N-dimethyl amino ethyl methacrylate benzyl chloride quaternary salt (available from Ciba Specialty Chemicals as AGEFLEX FM1Q80BC), N,N-dimethyl amino ethyl acrylate benzyl chloride quaternary salt (available from Ciba Specialty Chemicals as AGEFLEX FA1Q80BC), acrylic acid, methacrylic acid, itaconic acid, maleic acid, fumaric acid, crotonic acid, maleic anhydride and its half esters, and the half esters of phthalic anhydride with hydroxy functional alkyl (meth)acrylates, β-carboxy ethyl acrylate (available from Bimax Chemicals Ltd), 3-acrylamido-3-methyl-butanoic acid, 10-acrylamido-undecanoic acid, vinyl benzoic acid. Sulphonic, phosphonic or phosphoric acid-bearing monomers are also suitable, for example styrene, p-sulphonic acid (or the corresponding styrene p-sulphonyl chloride). Acid bearing monomers can be polymerised as the free acid or as a salt, for example, the ammonium or alkali metal salts of ethylmethacrylate-2-sulphonic acid (available from Laporte as Bisomer SEM), sodium 1-allyloxy-2-hydroxy propane sulphonate, 2-acrylamido-2-methylpropane sulphonic acid, sodium acrylate or the corresponding free acids. N,N-Dimethyl-N-(2-methacryloyloxyethyl)-N-(3-sulfopropyl)ammonium betaine (available from Raschig AG as SPE), N,N-Dimethyl-N-(3-methacrylamidopropyl)-N-(3-sulfopropyl)ammonium betaine (available from Raschig AG as SPP), 1-(3-Sulfopropyl)-2-vinylpyridinium betaine (available from Raschig AG as SPE). Vinyl esters such as vinyl acetate, vinyl propionate, vinyl laurate, and vinyl esters of versatic acid (available from Resolution Performance Products under the tradename VeoVa), vinyl ethers of heterocyclic vinyl compounds, alkyl esters of monoolefinically unsaturated dicarboxylic acids (such as di-n-butyl maleate and di-n-butyl fumarate) and, in particular, esters of acrylic acid and methacrylic acid, vinyl monomers with additional functionality for subsequent crosslinking of the co-polymers such as diacetone acrylamide, glycidyl methacrylate, aceto acetoxy ethyl methacrylate, 2-hydroxy ethyl (meth)acrylate, 4-hydroxy butyl(meth)acrylate, 3-hydroxy propyl(meth)acrylate, hydroxy stearyl (meth)acrylate, 2-hydroxyethyl(meth)acrylate and 2-(trimethylsiloxy)ethyl methacrylate may also be used.

A particularly preferred amphoteric co-polymer of the present invention is an acrylic co-polymer, based predominantly on acrylic or methacrylic monomers.

In Formula (1), optional unit [A] is derived from any olefinically unsaturated polymerisable monomer which does not contain an ionisable or ionised functional group. [B] provides the pendant polyether comb functionality of the amphoteric co-polymer. [C] provides the acidic functionality (unless [D] is a betaine salt in which case [C] is optional and v is equal to zero in Formula (1)) in the form of either free acid or salt and [D] provides the basic functionality in the form of either free amine, protonated amine salt, quaternised amine salt or betaine salt (when v=0).

The amphoteric co-polymer of Formula (1) comprises a backbone having pendant polyalkylene oxide, basic and acidic functionalities. The extent to which the acidic and basic units [C] and [D] respectively are present in either an ionised salt form or as free acid or base will depend on the pH value of the composition, the pKa values of the functional groups in the monomers from which [C] and [D] are derived and the relative amounts of basic unit [D] and acidic unit [C]. The $pK_a$ of the acidic component [F] in [C] is preferably less than 5.5. The $pK_a$ value of the basic substituent [E] in [D] is preferably in the range from 5.5 to 13.5. More preferably the $pK_a$ value of the basic substituent [E] in [D] is in the range from 8 to 12.

The $pK_a$ value for the basic substituent [E] in [D] is a measure of the acid strength of the conjugate acid [EH⁺] of the basic group [E], where $K_a$ is defined as:

$$K_a = Keq\,[H_2O] = \frac{[E]}{[EH^+][OH^-]}$$

and wherein $pK_a = -\log K_a$; and Keq is the equilibrium constant.

The amphoteric co-polymers of the present invention comprise [B] in the range from 5 to 95 weight %, more preferably from 10 to 90 weight % and most preferably from 15 to 80 weight %, and [A] in the range from 0 to 45 weight %.

Acidic unit [C] is preferably present in the range from 0 to 50 weight %, more preferably from 1 to 40 weight %.

Basic unit [D] is preferably present in the range from 1 to 50 weight %, more preferably from 1 to 40 weight %.

Preferably, the molar ratios of [A] to [B] to [C] to [D] (m:n:v:y) respectively, are chosen such that the cloud point of the amphoteric co-polymer is greater than 0° C. more preferably greater than 15° C. and most preferably greater than 25° C.

The cloud point value is related to the solubility of the polymer in water and refers to the boundary at which liquid-liquid phase separation takes place in a mixture of two or more components indicated by a cloudiness of the solution due to the formation of aggregates that scatter light. The temperature at which a 1% by weight solution of a polymer in distilled water becomes cloudy is the cloud point temperature.

The amphoteric co-polymers of the present invention preferably comprise from 5 to 95% by weight polyethylene oxide, more preferably from 10 to 80% by weight polyethylene oxide and especially from 15 to 70% by weight polyethylene oxide introduced by [B]. The exact level of polyethylene oxide introduced by [B] required to achieve a cloud point in the preferred range depends on a number of factors for example;

(i) The level and hydrophobicity of [A] in the amphoteric co-polymer.
(ii) The level and hydrophobicity of basic unit [D], and whether [D] is present as a free amine or in salt form in the amphoteric co-polymer.
(iii) The level and hydrophobicity of acidic unit [C] and whether [C] is present as free acid or in salt form in the amphoteric co-polymer.

(iv) The structure of [B] as defined by $R^2$, $R^3$, $R^4$, $R^5$ and the value of p in Formula (11).

(v) The presence of organics or electrolytes in solution.

It is preferred that the composition of anti-microbial agent and amphoteric co-polymer according to the present invention forms a clear solution, that is, the cloud point of the amphoteric co-polymer in the presence of anti-microbial agent (for example poly(hexamethylenebiguanide) (PHMB)) is above 15° C. and more preferably above 25° C.

Whilst the value of q is preferably 15 to 1000, q is most preferably 20 to 400.

Whilst $R^1$, $R^2$ and $R^3$ are each independently H, optionally substituted $C_{1-20}$-alkyl or $C_{3-20}$-cycloalkyl, it is preferred that $R^1$, $R^2$ and $R^3$ are each H, unsubstituted $C_{1-10}$-alkyl or $C_{3-8}$-cycloalkyl. Most preferably $R^1$ is H or $CH_3$, $R^2$ is H or $CH_3$, and $R^3$ is H or unsubstituted $C_{1-6}$-alkyl, especially H or $CH_3$.

$R^4$ and $R^5$ in repeating monomer units of [X] in Formula (10), may be the same or different, and each are independently H or $C_{1-4}$-alkyl so long as at least one of $R^4$ and $R^5$ is H. Preferably one of $R^4$ and $R^5$ is H and the other is —$CH_3$ or —$C_2H_5$ with the result that [X] comprises oxyethylene units or a mixture of oxyethylene, oxypropylene and/or oxybutylene units. Most preferably $R^4$ and $R^5$ are both H, with the result that [X] comprises oxyethylene units.

The value of p in Formula (10) is preferably from 3 to 50, more preferably from 3 to 40 and most preferably from 3 to 25.

T is an optionally substituted substitutent examples of which include CN, OH, F, Cl, Br, —$OR^6$, —$C(O)R^6$, —$OC(O)R^6$, —$C(O)OR^6$, —$C(O)NR^7R^8$ and aryl optionally substituted by —$OC(O)R^6$, F, Cl, Br, $C_{1-6}$-alkyl, —$CH_2Cl$ or —$C(O)OR^6$.

$R^6$ is $C_{1-10}$-alkyl more preferably $C_{1-8}$-alkyl for example methyl, ethyl, propyl, butyl, isopropyl, isobutyl or tert-butyl optionally substituted by a ketone, ether, epoxide, silane or ketoester group.

$R^7$ and $R^8$ are each independently H, $C_{1-8}$-alkyl or $C_{3-8}$-cycloalkyl optionally substituted by —OH, ketone or alkyl ether groups, most preferably $R^7$ and $R^8$ are H, —$CH_3$ or $C_2H_5$.

Preferably T is of the formula $C(O)OR^6$, —$C(O)NR^7R^8$ or —$OC(O)R^6$ and most preferably T is $C(O)OR^6$, wherein $R^6$, $R^7$ and $R^8$ are as previously described.

Each L is an optionally substituted linking group which joins [X] to the hydrocarbyl polymer backbone in Formula (10). L can be a variety of linking groups and maybe the same or different. Examples of L preferably comprise one or more carbon and/or hetero atoms, for example nitrogen or oxygen. Examples of preferred linking groups represented by L include:

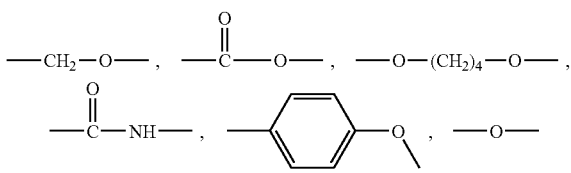

wherein the right hand side of the linking group is attached to [X] and the left hand side of the linking group is attached to the hydrocarbyl backbone.

It is particularly preferred that each L is of formula,

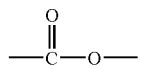

[J] is an optionally substituted hydrocarbyl group and may be the same or different. Examples of [J] (shown with reference to [G]) include:

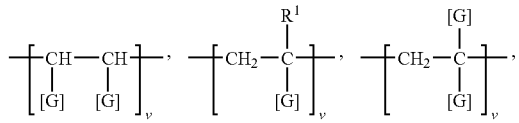

It is particularly preferred that [J] is of the Formula

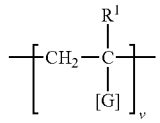

wherein $R^1$, v and [G] are as previously described.

[F] in Formula (12) is an acidic substitutent. Each [F] is joined either directly to the hydrocarbyl group [J] or is linked to [J] by one or more linking groups [G]. When w is 2 to 4 in Formula (12), [F] may be joined directly to [J] in which case b (representing the proportion of [G]) is zero. Alternatively, [F] may be joined to the same or different carbon atoms of [J] by [G]. [G] may be the same or different in the repeat units of [C].

When [G] is present, it is preferably selected from linking groups which directly bond to [J] or by linking groups with one or more groups of atoms each group of which provides a chain of one or more atoms for linking [F] with [J] with the proviso that only one [F] can be directly linked to a single carbon atom in [J].

In cases where [G] represents one or more groups of atoms, [G] provides a linking chain of atoms. The chain will normally comprise one or more carbon atoms (for example in the form of an alkyl and/or aryl group), which may be optionally substituted by hetero atoms such as —N, —O, —S or P, most preferably N or O.

Examples of [G] linking groups (shown with reference to [F]) include:

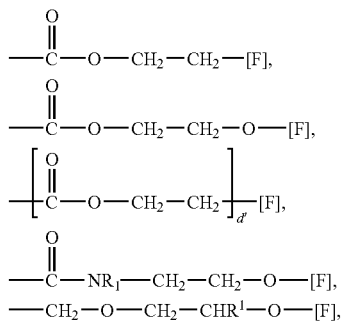

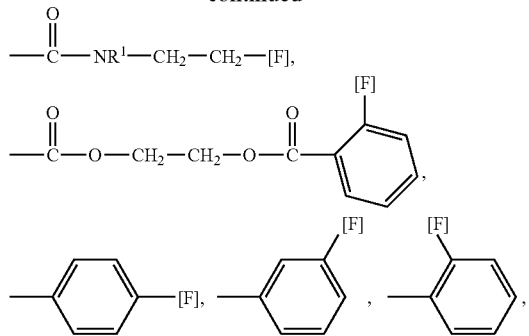

wherein d' is 2 or more, preferably 2, 3, 4 and 5 and F is the acidic substitutent.

It is preferred that [F] is linked directly to [J] or that [F] is linked to [J] by one of the following preferred linking groups represented by [G]:

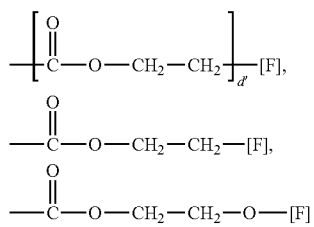

wherein d' and [F] are as previously described.

It is most especially preferred that [F] is linked directly to hydrocarbyl chain [J] in [C].

Examples of the acidic substitutent [F] in Formula (12) include carboxylic acid, sulphonic acid, phosphonic acid and phosphoric acid. It is preferred that [F] comprises a carboxylic acid.

[E] in Formula (13) is a basic substitutent and each [E] is joined either directly to the hydrocarbyl residue of [D] or is linked to it by an optionally substituted linking group [Z].

In cases where [Z] represents one or more groups of atoms, [Z] provides a linking chain of atoms. The chain will normally comprise one or more carbon atoms (in the form of an alkyl or aryl group) which may be optionally substituted by hetero atoms such as —N, —O, —S or P, preferably N or O.

Examples of linking groups represented by [Z] (shown with reference to [E]) include:

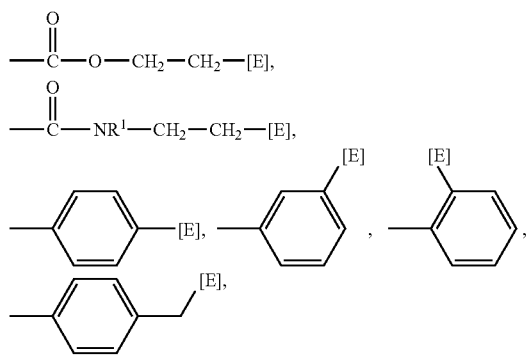

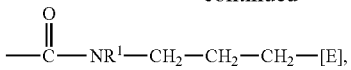

wherein $R^1$ and [E] are as previously described.

It is preferred that [E] is linked to the hydrocarbyl backbone of [D] by a linking group [Z] of the formula:

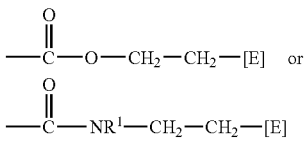

It is especially preferred that [E] is linked to the hydrocarbyl chain in [D] by a linking group [Z] represented by the formula:

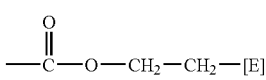

Therefore, it is preferred that s in [D] is 1.

Examples of the basic substitutent [E] in Formula (13) of [D] include: optionally substituted primary, secondary and tertiary aliphatic and aromatic amines, pyridine, imidazole, pyrazole, pyrimidine, pyrazine, pyrimidazine, tetrazole, 1,3,4-thiadiazole, 1,2,4-thiadiazole, pyrazole, 1,3,4-oxadiazole, 1,2,4-oxadiazole, pyrrole, 1,2,4-triazine, 1,3,5-triazine, pyrazine, pyridazine, indazole, indole and benzothiazole groups and the quaternised and protonated salts thereof. The definition of basic substitutent [E] used herein also includes quaternised salts and internal betaine salts.

It is preferred that [E] comprises a secondary or tertiary aliphatic amine or the protonated or quaternised salts thereof, for example (shown with reference to [Z]):

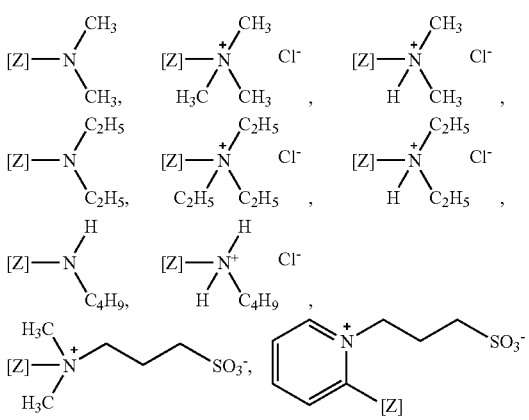

It is especially preferred that [E] comprises a tertiary aliphatic amine and the protonated or quaternised salts thereof, for example:

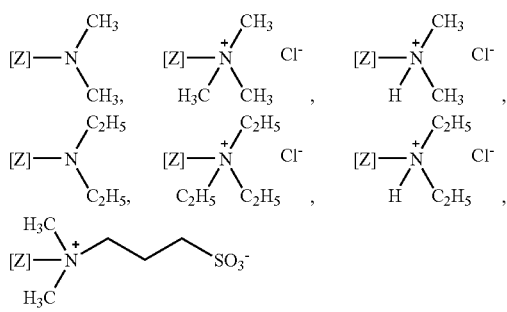

Examples of olefinically unsaturated monomers which may be used for [A] in Formula (1) include but are not limited to styrene, α-methyl styrene, acrylonitrile, methacrylonitrile, vinyl esters such as vinyl acetate, vinyl propionate, vinyl laurate, and vinyl esters of versatic acid such as VeoVa™ 9 and VeoVa™ 10 (available from Resolution Performance Products), vinyl ethers of heterocyclic vinyl compounds, in particular, esters of acrylic acid and methacrylic acid. Olefinically unsaturated monomers with additional functionality for subsequent crosslinking and/or adhesion promotion may also be used in the present invention to form [A]. Examples of such monomers include diacetone acrylamide, acetoacetoxy ethyl methacrylate, glycidyl methacrylate, 2-hydroxy ethyl (meth)acrylate, 4-hydroxy butyl(meth)acrylate, 3-hydroxy propyl(meth)acrylate, hydroxy stearyl(meth)acrylate and 2-hydroxy ethyl(meth)acrylate.

Examples of olefinically unsaturated monomers which may be used for [B] in Formula (1) include but are not limited to vinyl polyethers of ethylene or propylene oxide, for example hydroxypolyethoxy (5) polypropoxy (5) monoallyl ether (BX-AA-E5P5 available from Bimax Chemicals Ltd), methoxypolyethyleneglycol 350 methacrylate (available under the trade name from Laporte), methoxypolyethyleneglycol 550 methacrylate (available under the trade names Bisomer MPEG 350MA and Bisomer MPEG 550MA from Laporte), methoxypolyethyleneglycol 350 acrylate, polyethyleneglycol (6) methacrylate PEM6, polyethyleneglycol (6) acrylate PEA6.

Examples of olefinically unsaturated monomers which may be used for the anionic or acidic unit [C] in Formula (1) include but are not limited to acrylic acid, methacrylic acid, itaconic acid, maleic acid, fumaric acid, β-carboxy ethyl acrylate, sodium 1-allyloxy-2-hydroxy and propane sulphonate. Sulphonic, phosphonic or phosphoric acid-bearing monomers may also be used, such as styrene p-sulphonic acid (or the corresponding styrene p-sulphonyl chloride). The acid bearing monomers may be polymerised as the free acid or as a salt, for example the ammonium or alkali metal salts of ethylmethacrylate-2-sulphonic acid (available from Laporte as Bisomer SEM) or 2-acrylamido-2-methylpropane sulphonic acid.

Examples of olefinically unsaturated monomers which may be used for the cationic or basic unit [D] in Formula (1) include but are not limited to N,N-diethyl amino ethyl(meth) acrylate, N,N-dimethyl amino ethyl(meth)acrylate, N,N-dipropyl amino ethyl(meth)acrylate, N,N-diethyl amino ethyl (meth)acrylamide, N,N-dimethyl amino ethyl(meth) acrylamide, tertiary butyl amino ethyl methacrylate, N,N-dimethyl amino propyl(meth)acrylamide, N,N-dimethyl amino propyl(meth)acrylate, 4-vinyl pyridine, 2-vinyl pyridine, vinyl imidazole, N,N-dimethyl amino methyl styrene, 4-amino styrene, N,N-dimethyl amino styrene, amino methyl styrene. Basic amine bearing monomers can be polymerised as the free amine, as a protonated salt or quaternised amine salt, or as a betaine salt for example, basic quaternary ammonium monomers include N,N-dimethyl amino ethyl acrylate methyl chloride quaternary salt (available from Ciba Specialty Chemicals as AGEFLEX FA1Q80MC or from Mitsubishi Rayon Co. Ltd as DMCMA), N,N-dimethyl amino ethyl methacrylate benzyl chloride quaternary salt (available from Ciba Specialty Chemicals as AGEFLEX FM1Q80BC), N,N-dimethyl amino ethyl acrylate benzyl chloride quaternary salt (available from Ciba Specialty Chemicals as AGEFLEX FA1Q80BC), N,N-Dimethyl-N-(2-methacryloyloxyethyl)-N-(3-sulfopropyl)ammonium betaine (available from Raschig AG as SPE), N,N-Dimethyl-N-(3-methacrylamidopropyl)-N-(3-sulfopropyl)ammonium betaine (available from Raschig AG as SPP) and 1-(3-Sulfopropyl)-2-vinylpyridinium betaine (available from Raschig AG as SPE). [2-(methacryloyloxy)ethyl] dimethyl-(3-sulfopropyl)-ammonium hydroxide (available from Aldrich Chemicals, 3-(methacryloylamino)propyl dimethyl-(3 sulfopropyl)ammonium hydroxide (available from Aldrich Chemicals)

Preferred amphoteric co-polymers for use in the present invention are based on acrylic co-polymers, that is polymers based on acrylic or methacrylic esters. For preferred amphoteric co-polymers of the present invention [A], [B], [C] and [D] in Formula (1) have the Formulae (14), (15), (16) and (17) respectively. That is, [A] is of Formula (14),

Formula (14)

[B] is of Formula (15),

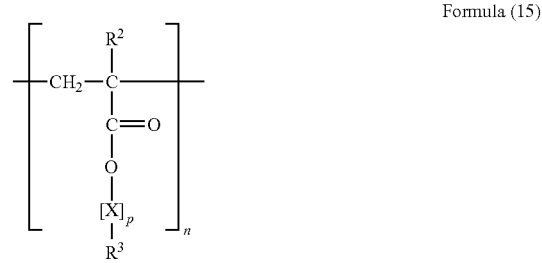

Formula (15)

[C] is of Formula (16), and

Formula (16)

[D] is of Formula (17),

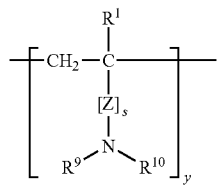

Formula (17)

wherein:

$R^6$ is $C_{1-10}$-alkyl more preferably $C_{2-4}$-alkyl optionally substituted by a ketone, ether, —OH, epoxide, silane or ketoester groups; and $R^9$ and $R^{10}$ may be the same or different and are each independently H, optionally substituted $C_{1-10}$-alkyl or $C_{3-8}$-cycloalkyl; and $R^1$, $R^2$, $R^3$, m, n, v, y, p, b, s, [G], [Z] and [X] are as hereinbefore defined.

Most preferably $R^9$ and $R^{10}$ are H or unsubstituted $C_{1-6}$-alkyl, especially unsubstituted $CH_3$ or $C_2H_5$.

When [D] is present as a quaternised salt it is preferably of Formula (18):

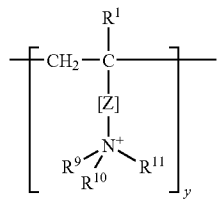

Formula (18)

$R^9$, $R^{10}$, Z, $R^1$ and s are previously hereinbefore described; and $R^{11}$ is optionally substituted $C_{1-10}$-alkyl, $C_{3-8}$-cycloalkyl. Most preferably, $R^{11}$ is unsubstituted $C_{1-10}$-alkyl or $C_{1-5}$-alkyl substituted by a sulphonate group, for example of the formula,

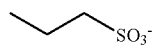

Preferred olefinically unsaturated monomers which may be used for [A] in Formula (14) include methyl acrylate, methyl methacrylate, ethyl acrylate, ethyl methacrylate, n-butyl acrylate, n-butyl methacrylate, 2-ethylhexyl acrylate, 2-ethylhexyl methacrylate, isopropyl acrylate, isopropyl methacrylate, iso butyl methacrylate, n-propyl acrylate, n-propyl methacrylate, t-butyl methacrylate, 2-ethylhexyl methacrylate, isobornyl methacrylate, cyclohexyl methacrylate and the corresponding acrylates. Methacrylates or acrylates having optional substitution at $R^6$ such as for example epoxide, alkyl ether, aryl ether, hydroxyalkyl, for example, hydroxyethyl, hydroxy propyl, hydroxy butyl and modified analogues may also be employed as part of [A] of Formula (14). Ketofunctional monomers for example acetoacetoxy esters of hydroxyalkyl acrylates and methacrylates for example acetoacetoxyethyl methacrylate, as well as silane functional monomers for example 2-(trimethylsiloxy)ethyl methacrylate may also be used. The advantages of using functionalised monomers is to provide subsequent crosslinkability or adhesion promotion in the resulting polymer.

Examples of the preferred acrylic monomers which may be used for [B] in Formula (15) include methoxypolyethyleneglycol 350 methacrylate and methoxypolyethyleneglycol 550 methacrylate (available under the trade name Bisomer MPEG 350MA and Bisomer MPEG 550MA from Laporte), methoxypolyethyleneglycol 350 acrylate, polyethyleneglycol (6) methacrylate PEM6 and polyethyleneglycol (6) acrylate PEA6.

Examples of preferred acrylic monomers which may be used for [C] in Formula (16) include methacrylic acid, acrylic acid and β-carboxy ethyl acrylate.

Examples of preferred acrylic monomers which may be used for [D] in Formula (17) include N,N-diethyl amino ethyl(meth)acrylate, N,N-dimethyl amino ethyl (meth)acrylate and the quaternised or protonated salts thereof.

As illustrated in Formula (1) the amphoteric co-polymers of the present invention comprise a vinyl backbone with pendant side-chains. The preferred amphoteric co-polymers of the present invention most preferably comprise from 0% to 45% by weight of [A], from 15% to 80% by weight of [B], from 1% to 40% of acidic [C] and from 1% to 40% of basic [D].

The amphoteric co-polymers used in the present invention may be prepared by any co-polymerisation method known in the art. Preferably, the co-polymerisation reaction is carried out in water, an organic solvent or a mixture of water and organic solvent using a free radical initiator. Suitable free-radical-yielding initiators include inorganic peroxides for example potassium, sodium or ammonium persulphate, hydrogen peroxide, or percarbonates; organic peroxides, for example acyl peroxides including for example benzoyl peroxide, alkyl hydroperoxides such as t-butyl hydroperoxide and cumene hydroperoxide; dialkyl peroxides such as di-t-butyl peroxide; peroxy esters such as t-butyl perbenzoate and mixtures thereof may also be used. The peroxy compounds are in some cases advantageously used in combination with suitable reducing agents (redox systems) such as sodium or potassium pyrosulphite or bisulphite, and iso-ascorbic acid. Azo compounds for example azoisobutyronitrile or dimethyl 2,2'-azo bis-isobutylate may also be used. Metal compounds such as iron.ethylenediaminetetracetic acid (EDTA) may also be usefully employed as part of the redox initiator system. Other free radical initiators include cobalt chelate complexes and particularly Co(II) and Co(III) complexes of porphyrins, dioximes and benzildioxime diboron compounds. It is also possible to use an initiator system partitioning between the aqueous and organic phases, for example a combination of t-butyl hydroperoxide, iso-ascorbic acid and iron.ethylenediaminetetracetic acid. Preferred initiators comprise azo compounds such as azo-iso-butyronitrile or dimethyl 2,2'-azo bis-isobutylate and peroxides for example hydrogen peroxide or benzoyl peroxide. The amount of initiator or initiator system conventionally used is for example within the range from 0.05 to 6 weight %, more preferably from 0.1 to 3% and most preferably from 0.5 to 2% based on the total amount of vinyl monomers used. The organic solvent is preferably a polar organic solvent and may be a ketone, alcohol or an ether. Examples of suitable polar solvents include methyl ethyl ketone, acetone, methyl isobutylketone, butyl acetate, ethoxyethylacetate, methanol, ethanol, n-propanol, iso-propanol, n-butanol, amyl alcohol, diethylglycol mono-n-butyl ether, butoxyethanol. Alternatively, the polar organic solvent may also be used with a non-polar organic liquid.

Suitable non-polar organic solvents include toluene-xylene mixtures and methylenechloride-dimethylformamide mixtures. Most preferably, the co-polymerisation reaction is carried out in aqueous alcoholic solvents for example, methanol, ethanol, n-propanol, iso-propanol, n-butanol, amyl alcohol, diethylglycol or butoxyethanol, most preferably aqueous ethanol mixtures.

When prepared by solution polymerisation the number average molecular weight (Mn) of the polymer is typically in the range 5,000 to 200,000, more preferably 10,000 to 100,000.

The amphoteric co-polymers can also be made by aqueous emulsion or suspension polymerisation (as described in *Principles of Polymerisation*, G Odian, Wiley, Interscience, $3^{rd}$ Edition, 1991), in which case the value of Mn may be much higher and in the range 20,000 to 500,000.

According to the present invention a preferred anti-microbial agent for use in a composition with an amphoteric co-polymer as previously described comprises an antibacterial agent, more preferably a linear polymeric biguanide which is a mixture of polymer chains in which the individual polymer chains, excluding the terminating groups are of Formula (6) or a salt thereof as hereinbefore described. A preferred linear polymeric biguanide for use in the present invention is poly(hexamethylenbiguanide) hydrochloride (PHMB) available from Avecia Limited under the trade name Vantocil™IB.

The amount of polymeric biguanide used in the composition of the present invention relative to the amount of amphoteric co-polymer is dependent upon the end use of the composition, the conditions under which it will be stored and the nature of the surface to which the composition is to be applied. The weight ratio of the linear polymeric biguanide to amphoteric co-polymer in the composition may vary over wide limits for example from 100:1 to 1:1000, more preferably from 20:1 to 1:500.

It is especially preferred that the ratio of linear polymeric biguanide group to amphoteric co-polymer in the anti-microbial composition is from 1:1 to 1:200.

The concentration of linear polymeric biguanide, for example poly(hexamethylene biguanide) (PHMB) used in the composition of the present invention is in the range from 0.001 weight % to 25 weight %, preferably from 0.005 weight % to 10 weight %, and especially from 0.01% to 5 weight %. The pH of the composition is typically chosen so that it is most appropriate for a particular application and is preferably in the range from pH 1 to 12 most preferably from pH 3 to 9.

The composition of the present invention may also contain other additives depending upon the particular use intended for the composition. Additional components optionally included in the composition maybe for example additional polymeric materials, detergents, botanical extracts, perfumes, fragrances, thickeners, humectants, anti-corrosion agents, surfactants, colourants, chelating agents, buffers, acidity and alkalinity regulators, wetting agents, sequestering agents, hydrotropes, adjuvants, anti-soil agents and enzymes.

For ease of handling and dosing, it is generally convenient to combine the linear polymeric biguanide and amphoteric co-polymer into a formulation with a suitable carrier. The carrier may be a solid but is preferably a liquid and the formulation is preferably a solution, suspension or emulsion of the anti-microbial composition in the liquid.

Whilst water is the preferred carrier for the composition, it is possible that other solvents such as water miscible organic solvents may also be present in the composition. Examples of suitable water-miscible organic solvents include glycols such as ethylene glycol, propylene glycol, dipropylene glycol, methanol, ethanol, propan-1-ol, propan-2-ol, $C_{1-6}$-alkyl esters for example butylethyl acetate, pentyl acetate, N-methyl-2-pyrrolidone and lower $C_{1-4}$-alkyl carbitols such as methyl carbitol. Preferred water-miscible organic solvents are glycols with 2 to 6 carbon atoms, poly-alkylene glycols with 4 to 9 carbon atoms or mono $C_{1-4}$-alkyl ethers of glycols with 3 to 13 carbon atoms. The most preferred water-miscible organic solvents are propylene glycol, ethyl hexyl glycol, ethanol, butyl ethyl acetate or pentyl acetate.

Therefore according to a second aspect of the present invention there is provided a formulation comprising:
(i) a linear polymeric biguanide;
(ii) an amphoteric co-polymer; and
(iii) a carrier.

A preferred formulation of the final diluted application liquor according to a second aspect of the invention comprises from 0.01 to 5% by weight linear polymeric biguanide, more preferably from 0.1 to 1% by weight linear polymeric biguanide in the form of poly(hexamethylene biguanide) hydrochloride (PHMB). The amount of amphoteric co-polymer in the formulation is preferably from 0.01 to 50% by weight, especially from 0.1 to 25% by weight. The preferred carriers are water or water/alcohol mixtures. The pH of the formulation is typically chosen to be most appropriate for the application and is preferably in the range from pH 1 to 12. Most preferably the pH of the formulation is in the range from 3 to 9. An especially preferred formulation according to the second aspect of the present invention comprises a diluted application solution containing from 0.5% by weight poly(hexamethylene biguanide) hydrochloride (PHMB) and from 2 to 15% by weight amphoteric co-polymer in the form of an aqueous solution.

The formulation may also contain other additives depending upon the particular use intended for the composition. Additional additives optionally included in the formulation are for example those listed in respect of the composition according to the first aspect of the present invention.

During the course of the present studies it has surprisingly been found that when a composition comprising a polymeric biguanide and an amphoteric co-polymer is applied to a surface a sustained anti-microbial effect against a broad range of micro-organisms including gram positive bacteria, gram negative bacteria, pathogenic bacteria, yeasts, fungi and algae. Therefore, according to a further aspect of the present invention there is provided a method of treating a surface which comprises treating the surface with a composition or a formulation as hereinbefore described with reference to the first and second aspects of the present invention.

The preferred anti-microbial agent, poly(hexamethylene biguanide) hydrochloride, may be the only microbiologically active compound present in the composition or formulation. Alternatively, other microbiologically active compounds may also be present in combination with the polymeric biguanides. Examples of other microbiologically active compounds include quaternary ammonium compounds for example, N,N-diethyl-N-dodecyl-N-benzylammonium chloride, N,N-dimethyl-N-octadecyl-N-(dimethyl benzyl)ammonium chloride, N,N-dimethyl-N,N-didecylammonium chloride, N,N-dimethyl-N,N-didodecylammonium chloride; N,N,N-trimethyl-N-tetradecylammonium chloride, N-benzyl-N,N-dimethyl-N-($C_{12}$-$C_{18}$ alkyl)ammonium chloride, N-(dichlorobenzyl)-N,-N-dimethyl-N-dodecylammonium chloride, N-hexadecylpyridinium chloride, N-hexadecyl pyridinium bromide, N-hexadecyl-N,N,N-trimethylammonium bromide, N-dodecyl pyridinium chloride, N-dodecylpyridinium bisulphate, N-benzyl-N-dodecyl-N,N-bis (beta-hydroxy-ethyl)ammonium chloride, N-dodecyl-N-benzyl-N,N-dimethylammonium chloride, N-benzyl-N,N- dimethyl-N-($C_{12}$-$C_{18}$ alkyl)ammonium chloride, N-dodecyl-N,N-dimethyl-N-ethylammonium ethylsulphate, N-dodecyl-N,N-dimethyl-N-(1-naphthylmethyl)ammonium chloride, N-hexadecyl-N,N-dimethyl-N-benzylammonium chloride, N-dodecyl-N,N-dimethyl-N-benzylammonium chloride or 1-(3-chloroallyl)-3,5,7-triaza-1-azonia-adamantane chloride, cocoalkylbenzyl-dimethylammonium, tetradecylbenzyldimethyl ammonium chlorides, myristyltrimethyl ammonium or cetyltrimethylammonium bromides, monoquaternary heterocyclic amine salts such as laurylpyridinium, cetylpyridinium or ($C_{12}$-$C_{14}$)alkyl benzylimidasolium chlorides; urea derivatives for example, 1,3-bis(hydroxymethyl)-5,5-dimethylhydantoin, bis(hydroxymethyl) urea, 3-(3,4-dichlorophenyl)-1,1-dimethylurea (Diuron), 3-(4-isopropylphenyl)-1,1-dimethylurea, tetrakis(hydroxymethyl)-acetylenediurea, 1-(hydroxymethyl)-5,5-dimethylhydantoin or imidazolidinylurea; amino compounds for example, 1,3-bis(2-ethyl-hexyl)-5-methyl-5-aminohexahydro-pyrimidine, hexamethylenetetramine, 1,3-bis(4-aminophenoxy)propane, dodecylamine or 2-[(hydroxymethyl)-amino]ethanol; imidazole derivatives for example 1[2-(2,4-dichloro-phenyl)-2-(2-propenyloxy)ethyl]-1H-imidazole or 2-(methoxycarbonylamino)-benzimidazole (Carbendazim); nitrile compounds for example, 2-bromo-2-bromomethylglutaronitrile, 2-chloro-2-chloro-methylglutaro-nitrile, 1,2-dibromo-2,4-dicyanobutane or 2,4,5,6-tetrachloro-1,3-benzenedicarbonitrile (Chlorothalonil); thiocyanate derivatives for example methylene(bis)thiocyanate or 2-(thiocyanomethylthio)-benzothiazole; tin compounds or complexes for example, tributyltinoxide chloride, naphthoate, benzoate or 2-hydroxybenzoate; isothiazolin-3-ones, for example 4,5-trimethylene-4-isothiazolin-3-one, 2-methyl-4,5-trimethylene-4-isothiazolin-3-one, 2-methyl-4-isothiazolin-3-one (MIT), 5-chloro-2-methyl-4-isothiazolin-3-one (CMIT), 2-octyl-isothiazolin-3-one (OIT) or 4,5-dichloro-2-octyl-4-isothiazolin-3-one (DCOIT); benzisothiazolin-3-one compounds for example 1,2-benzisothiazolin-3-one (BIT), 2-methylbenzisothiazolin-3-one, 2-n-butylbenzisothiazolin-3-one, N-ethyl, N-n-propyl, N-n-pentyl, N-cyclopropyl, N-isobutyl, N-n-hexyl, N-n-octyl, N-n-decyl and N-tert-butyl-1,2-benzisothiazolinone; thiazole derivatives for example, 2-(thiocyano methylthio)-benzthiazole or mercaptobenzthiazole; nitro compounds for example, tris(hydroxymethyl)nitromethane, 5-bromo-5-nitro-1,3-dioxane or 2-bromo-2-nitropropane-1,3-diol (Bronopol); iodine compounds, for example tri-iodo allyl alcohol; aldehydes and aldehyde release agents, for example glutaraldehyde (pentanedial), formaldehyde or glyoxal; amides for example chloracetamide, N,N-bis(hydroxymethyl)chloracetamide, N-hydroxymethyl-chloracetamide or dithio-2,2-bis(benzmethylamide); guanidine derivatives for example 1,6-hexamethylene-bis[5-(4-chlorophenyl)biguanide], 1,6-hexamethylene-bis[5-(4-chlorophenyl)guanide], bis(guanidinooctyl)amine triacetate, 1,6-D-(4'-chlorophenyldiguanide)-hexan (Chlorhexidine), polyoxyalkylene-guanidin-hydrochloride, polyhexamethyleneguanidine hydrochloride (PHMG), poly-(2-(2-ethoxy) ethoxyethyl guanidium chloride (PEEG) or dodecyl guanidine hydrochloride; thiones for example 3,5-dimethyltetrahydro-1,3,5-2H-thiodiazine-2-thione; sulphamides, for example N-dimethyl-N'-phenyl-(fluorodichloromethylthio)sulphamide (Preventol A4); triazine derivatives for example hexahydrotriazine, 1,3,5-tri-(hydroxyethyl)-1,3,5-hexahydrotriazine, 6-chloro-2,4-diethyl-amino-s-triazine or 4-cyclopropylamino-2-methylthio-6-t-butylamino-s-triazine (Irgarol); oxazolidine and derivatives thereof for example bis-oxazolidine; furan and derivatives thereof for example 2,5-dihydro-2,5-dialkoxy-2,5-dialkylfuran; carboxylic acids and the salts and esters thereof for example sorbic acid and 4-hydroxybenzoic acid; phenol and derivatives thereof for example 5-chloro-2-(2,4-dichlorophenoxy)phenol, thio-bis(4-chlorophenol), 2-phenylphenol, 2,4,5-trichloro-2'-hydroxy-diphenylether (Triclosan) and 4-chloro-3,5-dimethyl-phenol (PCMX); sulphone derivatives thereof for example diiodomethyl-paratolylsulphone, 2,3,5,6-tetrachloro-4-(methylsulphonyl)pyridine or hexachlorodimethylsulphone; imides for example, N-(fluorodichloromethylthio)phthalimide (Preventol A3), N-(trichloromethylthio)phthalimide (Folpet) or N-(trichloromethyl)thio-4-cyclohexene-1,2-dicarboxylmide (Captan); thioamides the metal complexes and salts thereof for example dimethyldithiocarbamate, ethylenebisdithiocarbamate, 2-mercapto-pyridine-N-oxide (especially the 2:1 zinc complex and the sodium salt); azole fungicides for example hexaconazole, tebuconazole, propiconazole, etaconazole or tetraconazole; strobilurins, for example methyl-(E)-2-[2-(6-(2-cyanophenoxy) pyrimidin-4-yloxy)phenyl]-3-methoxyacrylate (Azoxystrobin), methyl-(E)-methoxyimino[α-(o-tolyloxy)-o-tolyl]acetate, N-methyl-(E)-methoxyimino[2-(2,5-dimethlyphenoxymethyl) phenyl] acetamide, N-methyl-(E)-2-methoxyimino-2-(2-phenoxyphenyl)acetamide (Metominostrobin) or Trifloxystrobin; amides for example dithio-2,2'-bis(benzmethylamide) (Densil P) or 3,4,4'-Trichlorocarbanilide (Triclocarban); carbamates for example 3-Iodopropargyl-N-butylcarbamate (IPBC), 3-Iodopropargyl-N-phenylcarbamate (IPPC) or Bis-(diemthylthiocarbamoyl)-disulphide (Thiram); pyridine derivatives for example sodium or zinc salt of 2-mercaptopyridine-N-oxide (Sodium or Zinc pyrithione); compounds with activated halogen groups for example tetrachloroisophthalodintril (Chlorthalonil), 1,2-Dibromo-2,4-dicyanobutane (Tektamer 38); organometallic compounds for example 10,10'-Oxybisphenoxyarsine (OBPA).

The amount of additional anti-microbial compound(s) in the composition will depend upon the nature of the additional anti-microbial compound and the surface to be protected against microbial degradation.

It is further possible to use combinations of two or more amphoteric co-polymers of Formula (1) as previously described with the anti-microbial compounds as previously described for the compositions or formulations of the present invention for disinfecting surfaces found in for example household, industrial or institutional areas. The treatment can be applied to a wide variety of surfaces as exemplified as follows but not limited thereto. Surface applications include for example walls, floors, work surfaces, equipment found in domestic, industrial, food processing, sanitary, health and medical environments, skin, synthetic and natural textiles and fibres, stainless steel, polymer and polymeric coatings such as vinyl, polyvinyl chloride, polypropylene and polyethylene, wood, glass, rubber, paint surfaces, stone, marble, grouts, packaging and films.

As hereinbefore described the anti-microbial compositions according to the first and second aspects of the invention significantly reduce the levels of micro-organisms on surfaces treated with the anti-microbial compositions, which activity is sustained over a period of time.

According to a fourth aspect of the present invention there is therefore provided the use of a composition according to the first aspect of the present invention or the use of a formulation according to a second aspect of the present invention for the treatment of surfaces.

It has also been found that the amphoteric co-polymers according to the present invention may also be used in combination with anti-fungal compounds. It has surprisingly been found that fungicidal compounds are also controllably released from the amphoteric co-polymers over time thereby providing sustained and effective anti-fungal control.

Fungicides

A wide variety of fungicides can be used in combination with the amphoteric co-polymers described above. Examples of such fungicides include but are not limited to: methoxyacrylates, for example, methyl (E)-2-2-6-(2-cyanophenoxy)pyrimidin-4-yloxyphenyl-3-methoxyacrylate; carboxamides and acetamides for example, 5,6-dihydro-2-methyl-N-phenyl-1,4-oxathiin-3-carboxamide and 2-cyano-N-[(ethylamino)carbonyl]-2-(methoxyamino)acetamide; aldehydes, for example cinnamaldehyde and 3,5-dichloro-4-hydroxybenzaldehyde; pyrimidines, for example 4-cyclopropyl-6-methyl-N-phenyl-2-pyrimidinamine and 5-butyl-2-ethylamino-6-methylpyrimidin-4-ol; morpholines for example, (E,Z)-4-[3-(4-chlorophenyl)-3-(3,4-dimethoxyphenyl)acryloyl]morpholine and $C_{11-14}$-alkyl-2,6-dimethylmorpholine-homologues such as (Tridemorph) and (±)-cis-4-[3-tert-butylphenyl)-2-methylpropyl]-2,6-dimethylmorpholine (Fenpropimorph); guanidines, for example 1-dodecylguanidine acetate; pyrroles, for example 4-(2,2-difluoro-1,3-bezodioxol-4-yl)-1Hpyrrole-3-carbonitrile; imidazoles and benzimidazoles, for example 1-[2-(2,4-dichlorophenyl)-2-(2-propenyloxy)ethyl]-1H-imidazole, 3-(3,5-dichlorophenyl)-N-(1-methylethyl)-2,4-dioxo-1-imidazolidinecarboxamide, Carbendazim (MBC), Benomyl, Fuberidazole, Thiabendazole, 1-(N-propyl-N-(2-(2,4,6-(trichlorophenoxy)-ethyl)-carbamoyl)-imidazole (prochloraz) and salts thereof; alanine derivatives for example, N-(2,6-dimethylphenyl)-N-(methoxyacetyl)-D-alaninemethyl ester and N-(2,6-dimethylphenyl)-N-(methoxyacetyl)-DL-alaninemethyl ester; triazoles for example, 1-[[2-(2,4-dichlorophenyl)-4-propyl-1,3-dioxolan-2-yl]methyl]-1H-1,2,4-triazole, H-1,2,4-triazole-1-ethanol-alpha-[2-(4-chlorophenyl)-ethyl]-alpha-(1,1-dimethylethyl),1-[2-(2,4-dichlorophenyl)-1,3-dioxolan-2-yl-methyl]-1H-1,2,4-triazole [azaconazole], 1-(4-chlorophenoxy)-3,3-dimethyl-1-(1H-1,2,4-triazol-1-yl)-2-butanone (triadimefone), β-(4-chlorophenoxy)-α-(1,1-dimethyl-ethyl)-1H-1,2,4-triazole-1- ethanol (triadimenol), α-[2-(4-chlorophenyl)-ethyl]-α-(1,1-dimethylethyl)-1H-1,2,4-triazole-1-ethanol (tebuconazole), (RS)-2-(2,4-dichlorophenyl)-1-(1H-1,2,4-triazol-2-yl)-hexan-2-ol (hexaconazole), 1-[[2-(2,4-dichlorophenyl)-4-n-propyl-1,3-dioxolan-2-yl]-methyl]-1-H-1,2,4-triazole (propiconazole). Triazole fungicides can be present not only in the form of free bases but also in the form of their metal salt complexes or as acid addition salts, for example salts of metals of main groups II to IV and sub-groups I and II and IV to VII of the periodic table of elements, examples of which may include copper, zinc, manganese, magnesium, tin, iron, calcium, aluminium, lead, chromium, cobalt and nickel. Possible anions of the salts are those which are preferably derived from the following acids: hydrohalic acids, for example, hydrochloric acid, hydrobromic acid, phosphoric acid, nitric acid and sulphuric acid. In cases where the compound has an asymmetric carbon atom, isomers and isomer mixtures are also possible. Further examples of fungicides include: oxazolidines for example, 3-(3,5-dichlorophenyl)-5-methyl-5-vinyl-1,3-oxazolidine-2,4-dione; p-hydroxybenzoates for example, benzoic acid, paramethylbenzoic acid, salicylic acid, dehydroacetic acid and salts thereof; isothiazolinones, for example 2-methyl-isothiazolin-3-one, 5-chloro-2-methylisothiazolin-3-one, 4,5-dichloro-N-octyl-isothiazolin-3-one, 2-n-octyl-4-isothiazolin-3-one, cyclopentenisothiazolinones; benzisothiazolin-3-one compounds for example 2-methylbenzisothiazolin-3-one, 2-n-butylbenzisothiazolin-3-one N-ethyl, N-n-propyl, N-n-pentyl, N-n-hexyl, N-cyclopropyl, and N-isobutylbenzisothiazolin-3-one; quaternary ammonium compounds for example, cocoalkylbenzyldimethylammonium, tetradecylbenzyldimethylammonium chlorides, myristyltrimethyl ammonium, cetyltrimethylammonium bromides, monoquaternary heterocyclic amine salts, laurylpyridinium, cetylpyridinium or ($C_{12}$-$C_{14}$)alkyl benzylimidasolium chlorides, benzyldimethyltetradecylammoniumchloride, benzyl-dimethyl-dodecylammoniumchloride, didecyl-dimethyl-ammoniumchloride, alkyl ammonium halides, for example lauryl trimethyl ammonium chloride and dilauryl dimethyl ammonium chloride, alkyl aryl ammonium halides such as octadecyl dimethyl benzyl ammonium bromide, ethyl dimethyl stearyl ammonium chloride, trimethyl stearyl ammonium chloride, trimethyl cetyl ammonium chloride, dimethyl ethyl lauryl ammonium chloride, dimethyl propyl myristyl ammonium chloride, dinonyl dimethyl ammonium chloride, didecyl dimethyl ammonium chloride, diundecyl dimethyl ammonium chloride, didecyl dimethyl ammonium chloride, dinonyl)ethyl ammonium chloride, dimethyl ethyl benzyl ammonium chloride, 3-(trimethyxyosilyl)propyldidecylmethyl ammonium chloride, 3-(trimethyoxysilyl)propyloctadecycdimethyl ammonium chloride, dimethyl dioctyl ammonium chloride, didecyl dimethyl ammonium chloride, didodecyl dimethyl ammonium chloride, dimethyl ditetradecyl ammonium chloride, dihexadecyl dimethyl ammonium chloride, dimethyl dioctadecyl ammonium chloride, decyl dimethyl octyl ammonium chloride, dimethyl dodecyloctyl ammonium chloride, benzyl decyl dimethyl ammonium chloride, benzyl dimethyl dodecyl ammonium chloride, benzyl dimethyl tetradecyl ammonium chloride, decyl dimethyl(ethyl benzyl)ammonium chloride, decyl dimethyl(dimethyl benzyl)-ammonium chloride, (chlorobenzyl)-decyl dimethyl ammonium chloride, decyl-(decyl-(dichlorobenzyl)-dimethyl ammonium chloride, benzyl didecyl methyl ammonium chloride, benzyl didocyl methyl ammonium chloride, benzyl ditetradecyl methyl ammonium chloride, and benzyl dodecyl ethyl ammonium chloride; iodopropargyl derivatives for example, 3-iodo-2-propynyl-N-n-butylcarbamate (IPBC), propyl 3-(dimethylamino)propylcarbamate-hydrochlorides, 3-iodo-2-propynyl-N-n-propyl carbamate, 3-iodo-2-propynyl-N-n-hexyl carbamate, 3-iodo-2-propynyl-N-cycohexylcarbamate, 3-iodo-2-propynyl-N-phenyl carbamate and thiocarbamates for example S-ethyl cyclohexyl(ethyl)thiocarbamate; sulphenamides for example, Dichlofluanid (Euparen), Tolylfluarid (Methyleuparen), Folpet, Fluorfolpet, tetramethyldiuramdisulfides (TMTD) and 2-methylbenzamide-1,1'disulphide (available as Densil™P from Avecia Ltd); thiocyanates for example, thiocyanatomethylthiobenzothiazole (TCMTB) and methylenbisthiocyanate (MBT); phenols for example, o-phenylphenol, tribromphenol, tetrachlorphenol, pentachlorphenol, 2-phenoxyethnaol 3-methyl-4-chlorphenol, dichlorophen and chlorophen; iododeriatives for example, diiodmethyl-p-arylsulfone and diiodmethyl-p-tolylsulfone; bromoderivatives for example, 2-bromo-2-nitro-1,3-propanediol(Bronopol) and 1,2-dibromo-2,4-dicyanobutane (Tektamer™38); pyridines for example, 1-hydroxy-2-pyridinthione or pyridine-2-thiol-1-oxide (sodium, iron, manganese or zinc salts commercially available under the trademark Sodium Omadine from Arch Chemicals), tetrachlor-4-methylsulphonylpyridine, 2,3,5,6 tetrachloro-4(methyl sulphonyl)pyridine (available from Avecia Limited as Densil™ S); metallic soaps for example, tin, copper, zinc-naphthenate, octoate, 2-ethylhexanoate, oleate, -phosphate, benzoate, or oxides for example TBTO, $Cu_2O$, CuO and ZnO; organic tin-derivatives, for example tributyltin naphthenate or tributyl tinoxide; dialkyldithiocarbamates for example sodium and zinc salts of dialkyldithiocarbamates; nitrites for example 2,4,5,6-tetrachlorisophthalonitrile (Chlorthalonil); benzthiazoles, for example 2-mercaptobenzothiazoles; Dazomet; chinolines for example 8-hydroxyquinoline; Tris-N-(cyclohexyldiazeniumdioxy)-aluminum, N-(cyclohexyldiazeniumdioxy)-tributyl tin or potassium salts and Bis-(N-cyclohexyl)diazinium (-dioxy- copper or aluminum); alkyl esters of parahydroxybenzoic acid particularly the methyl, ethyl, propyl and; 2,4,4'-trichloro-2-hydroxydiphenyl ether (available under the trade name Triclosan) or 4,4'-trichloro-2-hydroxydiphenyl ether available under the tradename Diclosan); formaldehyde release compounds for example hydantoins, N,N"-methylene bis[N'-(hydroxymethyl)-2,5-dioxo-4-imidazolidinyl]urea, Quaternium-15 and 1,3-dimethylol-5,5-dimethylhydantoin (DMDMH), N-(hydroxymethyl)-N-(1,3-dihydroxymethyl-2,5-dioxo-4-imidazolidinyl)-N'-(hydroxymethyl); urea and the cis isomer of 1-(3-chloroallyl)-3,5,7-triaza-1-azoniaadamantane chloride; benzylalcoholmono(poly)hemiformal, oxazolidine, hexahydro-s-triazine and N-methylolchloracetamid; cyclic thiohydroxamic acid compounds for example imidazolidine-2-thione, pyrrolinethione, pyrrolidinethione, isoindolinethione, 3-hydroxy-4-methylthiazol-2(3H)-thione, 3-hydroxy-4-phenylthiazol-2(3H)-thione, 3-hydroxy-4,5,6,7-tetrahydrobenzothiazol-2(3H)-thione, 5,5-dimethyl-1-hydroxy-4-imino-3-phenylimidazolidine-2-thione, 1-hydroxy-4-imino-3-phenyl-2-thiono-1,3-diazaspiro[4,5]-decane, 1-hydroxy-5--methyl-4-phenylimidazoline-2-thione, 4,5-dimethyl-3-hydroxythiazol-2(3H)-thione, 4-ethyl-3-hydroxy-5-methylthiazol-2(3H)-thione, 4-(4-chlorophenyl)-3-hydroxythiazol-2(3H)-thione, 3-hydroxy-5-methyl-4-phenylthiazol-2(3H)-thione, 1-hydroxypyrrolidin-2-thione, 5,5-dimethyl-1-hydroxypyrrolidin-2-thione and 2-hydroxy-2,3-dihyro-1H-isoindol-1-thione.

Preferred antifungal compounds include quaternary ammonium compounds, isothiazolione and benzisothiazolinone compounds, carbamates and pyridine compounds.

Therefore, according to a fifth aspect of the present invention there is provided a composition comprising:
(i) a fungicide; and
(ii) an amphoteric co-polymer of the Formula (1):

  Formula (1)

wherein
[A] is of Formula (9),

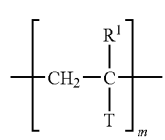  Formula (9)

[B] is of Formula (10),

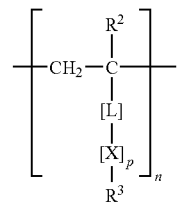  Formula (10)

[C] is of Formula (12),

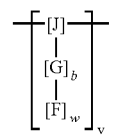  Formula (12)

[D] is of Formula (13),

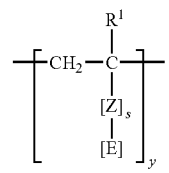  Formula (13)

and X is of Formula (11),

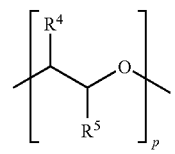  Formula (11)

wherein [A], [B], [C] and [D] may occur in any order;
T is an optionally substituted substitutent;
L, G and Z each independently is an optionally substituted linking group;
$R^1$, $R^2$ and $R^3$ are each independently H, optionally substituted $C_{1-20}$-alkyl or optionally substituted $C_{3-20}$-cycloalkyl;
$R^4$ and $R^5$ are each independently H or $C_{1-4}$-alkyl;
q is 15 to 1000;
p is 3 to 50;
J is an optionally substituted hydrocarbyl group;
F is an acidic substitutent;
E is a basic substitutent;
m is 0 to 350;
n is 1 to 75;
v is 0 to 100;
y is 1 to 100;
b is 0, 1 or 2;
s is 0 or 1;
w is 1 to 4; and provided that at least one of $R^4$ and $R^5$ is H.

In the fifth aspect of the present invention preferences for [A], [B], [C], [D], m, n, v, y, q, T, L, X, J, G, F, Z, E, p, b, w, s, $R^1$, $R^2$, $R^3$, $R^4$ and $R^5$ are as hereinbefore defined with reference to the first aspect of the present invention.

The invention is further illustrated by the following examples in which all parts are by weight unless otherwise stated.

Experimental Details

1. Preparation of Amphoteric Co-Polymers.

The Preparation of Polymer Example 2 (Table 1) an Amphoteric Co-Polymer.

A clean dry 2 L glass reactor was fitted with an overhead stirrer, nitrogen bleed, thermocouple and condenser. An initiator solution (1) was prepared by dissolving dimethyl 2,2' azobis isobutyrate (2.1 g, 0.009 moles) in solvent (96.1 g of a 50/50 mixture of ethanol/distilled water). A monomer solution (2) containing solvent (247.6 g of a 50/50 mixture of ethanol/distilled water), methacrylic acid (25.8 g, 0.3 moles), dimethylaminoethylmethacrylate (47.2 g, 0.3 moles) and methoxy(polyethylene glycol 350) monomethacrylate (130.5 g, 0.3 moles) was prepared. Monomer solution (2) was added to the reactor along with additional solvent (378 g of a 50/50 mixture of ethanol/distilled water). The monomer solution washed into the reactor with further additional solvent (100 g of a 50/50 mixture of ethanol/distilled water). The reactor was heated to 75° C. using a Haake circulating water bath and was stirred at 180 rpm under a nitrogen blanket. At time zero 24.5 g of initiator solution (1) was added to the reactor followed 30 minutes later by 49.1 g of initiator solution (1). The reaction mixture was left for 3 hours 30 minutes before increasing the reactor temperature to 80° C. On reaching the required temperature 12.3 g of initiator solution (1) was added to the reactor and allowed to continue for a further two hours after which the final aliquot 12.3 g of initiator solution (1) was added. After a further two hours the polymer solution was cooled and removed from the reactor.

The total time of polymerisation was eight hours. The final solution was water white and free of particulate matter. The co-polymer was formed in greater than 99% yield as determined by weight difference following exhaustive evaporation from a sample of the polymer solution.

The molecular weight of the co-polymer was determined using gel permeation chromatography (GPC) with polyethylene oxide used as molecular weight standards. NMR analysis was used to confirm the ratio of the monomer repeat units [A], [B], [C] and [D]. Dynamic Mechanical Thermal Analysis (DMTA) was used to determine the Tg of the copolymer.

Polymers 1 to 23 in Table 1, containing different monomers [A], [B], [C] and [D] in various molar ratios, were prepared according to the same procedure as outlined above.

TABLE 1

Composition of Amphoteric co-polymers.

| Example Number | Monomers | | | | Molar Ratio of Repeat Units [A]:[B]:[C]:[D] | | | |
|---|---|---|---|---|---|---|---|---|
| | [A] | [B] | [C] | [D] | [A] | [B] | [C] | [D] |
| 1 | MMA | PEG150MA | MAA | DMAEMA | 4 | 1 | 1 | 1 |
| 2 | | PEG350MA | MAA | DMAEMA | | 1 | 1 | 1 |
| 3 | | PEG350MA | MAA | DMAEMA | | 1 | 1.5 | 1.5 |
| 4 | | PEG350MA | MAA | DMAEMA | | 1 | 1 | 2 |
| 5 | | PEG550MA | MAA | DMAEMA | | 1 | 1 | 1 |
| 6 | | PEG550MA | MAA | DMAEMA | | 1 | 1.5 | 1.5 |
| 7 | | PEG550MA | MAA | DMAEMA | | 1 | 1 | 2 |
| 8 | | PEG550MA | MAA | DMAEMA | | 1 | 2 | 1 |
| 9 | | PEG550MA | MAA | DMAEMA | | 1 | 2 | 2 |
| 10 | MMA | PEG350MA | MAA | DMAEMA | 2 | 1 | 1 | 1 |
| 11 | MMA | PEG350MA | MAA | DMAEMA | 4 | 1 | 1 | 1 |
| 12 | MMA | PEG350MA | MAA | DMAEMA | 6 | 1 | 1 | 1 |
| 13 | MMA | PEG350MA | MAA | DMAEMA | 8 | 1 | 1 | 1 |
| 14 | EMA | PEG350MA | MAA | DMAEMA | 2 | 1 | 1 | 1 |
| 15 | iBMA | PEG350MA | MAA | DMAEMA | 2 | 1 | 1 | 1 |
| 16 | BMA | PEG350MA | MAA | DMAEMA | 2 | 1 | 1 | 1 |
| 17 | IBnM | PEG350MA | MAA | DMAEMA | 2 | 1 | 1 | 1 |
| 18 | MMA | PEG350MA | MAA | DMAEMA | 2 | 1 | 1 | 2 |
| 19 | MMA | PEG550MA | MAA | DMAEMA | 2 | 1 | 1 | 1 |
| 20 | MMA | PEG550MA | MAA | DMAEMA | 4 | 1 | 1 | 1 |
| 21 | MMA | PEG550MA | MAA | DMAEMA | 7.5 | 1 | 1 | 1 |
| 22 | MMA | PEG550MA | MAA | DMAEMA | 2 | 1 | 1.5 | 1.5 |
| 23 | Styr | PEG550MA | MAA | DMAEMA | 2 | 1 | 1.5 | 1.5 |
| 24 | | PEG350MA | MAA | pAminoSTY | | 1 | 1 | 1 |
| 25 | | PEG350MA | AMPS | DMAEMA | | 1 | 1 | 1 |
| 26 | MMA | PEG350MA | | AMPHO1 | 4 | 1 | | 1 |
| 27 | MMA | PEG350MA | | AMPHO2 | 4 | 1 | | 1 |
| 28 | MMA | PPG5MA | MAA | DMAEMA | 2 | 1 | 1 | 1 |
| 29 | MMA | PPG5MA | MAA | DMAEMA | 2 | 1 | 1 | 2 |
| 30 | iBMA | PPG5MA | MAA | DMAEMA | 2 | 1 | 1 | 2 |
| 31 | iBMA | PEG350MA | MAA | DMAEMA | 3 | 1 | 1 | 1 |

TABLE 1-continued

| 32 | iBMA | PEG350MA | MAA | DMAEMA | 4 | 1 | 1 | 1 |
| 33 | iBMA | PEG550MA | MAA | DMAEMA | 2 | 1 | 1 | 1 |

| | |
|---|---|
| MAA | Methacrylic Acid |
| BMA | Butyl methacrylate |
| iBMA | iso-Butyl methacrylate |
| Styr | Styrene |
| EMA | Ethyl methacrylate |
| iBnM | iso-Bornyl methacrylate |
| DMAEMA | Dimethylaminoethylmethacrylate |
| AMPS | 2-acrylimidomethylpropane sulphonic acid |
| p-AminoSTY | p-amino styrene |
| AMPHO 1 | [2-(methacryloyloxy) ethyl] dimethyl-(sulfopropyl) ammonium hydroxide |
| AMPHO 2 | 3-(methacryloylamino) propyl dimethyl-(3 sulfopropyl) ammonium hydroxide |
| PPG5MA | Methoxy polypropylene glycol monomethacrylate with 5 propylene oxide units |
| PEG150MA | Methoxy polyethylene glycol monomethacrylate with 3 to 4 ethylene oxide units. |
| PEG350MA | Methoxy polyethylene glycol monomethacrylate with 7 to 8 ethylene oxide units. |
| PEG550MA | Methoxy polyethylene glycol monomethacrylate with 12 to 13 ethylene oxide units. |

Determination of the Cloud Points of Amphoteric Co-Polymers of Table 1 and Cloud Point Changes with Polymer Composition.

The cloud points of the amphoteric co-polymers in Table 1 were determined by making 1% by weight solutions of the polymers in distilled water. Each polymer solution was heated and stirred until it became cloudy. The stirred solution was then allowed to cool whilst the temperature was monitored. The temperature at which the solution became clear is the cloud point. The cloud point of Polymer 2 determined by this method was greater than 98° C. (polyethylene oxide content 60 w/w %).

FIG. 1 shows how the cloud point varies as a function of the methyl methacrylate content in Polymers 20, 21 and 22.

From FIG. 1 it can be concluded that as the polymer becomes more hydrophobic as a result of an increase in the MMA content and decrease in methoxy polyethylene glycol monomethacrylate (PEG) content the cloud point decreases.

Figure 2:
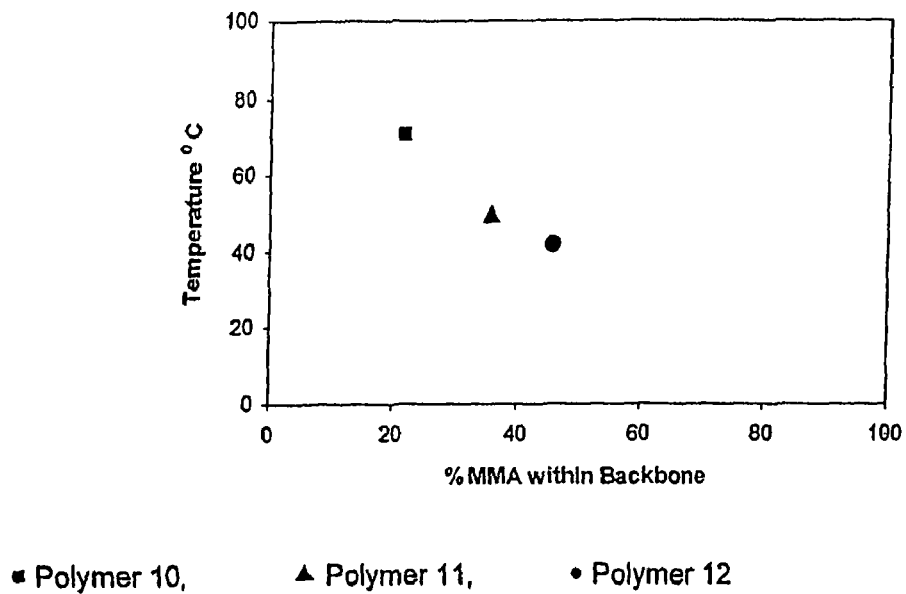
FIG. 2 shows a graph of the polymer cloud point variation as a function of methyl methacrylate in polymers 10, 11 and 12.

From FIG. 2 it can be concluded that as the polymer becomes more hydrophobic as a result of the increase in MMA content and a decrease in the PEG content the cloud point decreases.

Preparation of Amphoteric Co-Polymer/Antimicrobial Agent Compositions.

Compositions 1 to 104 were prepared by mixing a 20% aqueous solution of poly (hexamethylene biguanide) hydrochloride (PHMB) (5g) (available from Avecia Limited as Vantocil™ IB) to each of the polymers 1 to 33 from Table 1 as 20% solutions (either in water/ethanol 1/1 or water) in varying quantities as set out in Table 2. The compositions were allowed to stand for 24 hours before being applied to substrates such as glass or ceramic tiles. All of the compositions were low viscosity colourless transparent solutions, free from sediment and with excellent storage stability. Storage stability was tested by storing the compositions for 2 months at 52° C. and was considered excellent if the viscosity of the composition remained unchanged and there was no formation of precipitate or gel particles.

Preparation of basic Copolymer compositions with various biocides looking at antifungal properties using polymer Example 15.

Compositions 105-112 were prepared by mixing with various biocides. To a sample of the polymer solution the biocide was added at concentrations ranging from 0.1%-0.5% wt/wt on total weight of the solution. The compositions were placed on a rotating mixer for 24 hours to form a homogenious composition and then applied to substrates such as glass or ceramic tile. The compositions were of low viscosity and free from sediment.

TABLE 2

Amphoteric co-polymer/PHMB Compositions.

| Composition Number | Amphoteric co-polymer Number* | Amphoteric co-polymer (wt %) | Polymeric Biguanide (PHMB)/other Biocide (wt %) |
|---|---|---|---|
| 1 | 1 | 95 | 5 |
| 2 | 2 | 39.4 | 60.6 |
| 3 | 2 | 50 | 50 |
| 4 | 2 | 75 | 25 |
| 5 | 2 | 77.1 | 22.9 |
| 6 | 2 | 83.3 | 16.7 |
| 7 | 2 | 94.2 | 5.8 |
| 8 | 2 | 95 | 5 |
| 9 | 3 | 33.7 | 66.3 |
| 10 | 3 | 44.6 | 56.4 |
| 11 | 3 | 71.8 | 28.2 |
| 12 | 3 | 75 | 25 |
| 13 | 3 | 92.7 | 7.3 |
| 14 | 3 | 95 | 5 |
| 15 | 4 | 44.4 | 56.4 |
| 16 | 4 | 79.4 | 20.6 |
| 17 | 4 | 95. | 5.0 |
| 18 | 4 | 95.1 | 4.9 |
| 19 | 5 | 50 | 50 |
| 20 | 5 | 80 | 20 |
| 21 | 5 | 83.3 | 16.7 |
| 22 | 5 | 95 | 5 |
| 23 | 5 | 95.2 | 4.8 |
| 24 | 6 | 90 | 10 |
| 25 | 6 | 95 | 5 |
| 26 | 7 | 48.5 | 51.5 |
| 27 | 7 | 75 | 25 |
| 28 | 7 | 82.5 | 17.5 |
| 29 | 7 | 95 | 5 |
| 30 | 7 | 95.9 | 4.1 |
| 31 | 8 | 30.6 | 69.4 |
| 32 | 8 | 60.7 | 31.3 |
| 33 | 8 | 91.6 | 8.4 |
| 34 | 8 | 95 | 5 |
| 35 | 9 | 37.1 | 62.9 |
| 36 | 9 | 74.8 | 25.2 |
| 37 | 9 | 75 | 25 |

TABLE 2-continued

Amphoteric co-polymer/PHMB Compositions.

| Composition Number | Amphoteric co-polymer Number* | Amphoteric co-polymer (wt %) | Polymeric Biguanide (PHMB)/other Biocide (wt %) |
|---|---|---|---|
| 38 | 9 | 93.7 | 6.3 |
| 39 | 9 | 95 | 5 |
| 40 | 10 | 45.6 | 54.4 |
| 41 | 10 | 75 | 25 |
| 42 | 10 | 80.7 | 19.3 |
| 43 | 10 | 90 | 10 |
| 44 | 10 | 95 | 5 |
| 45 | 10 | 95.4 | 4.6 |
| 46 | 11 | 50.4 | 49.6 |
| 47 | 11 | 75 | 25 |
| 48 | 11 | 83.6 | 16.4 |
| 49 | 11 | 90 | 10 |
| 50 | 11 | 95 | 5 |
| 51 | 11 | 96.2 | 3.8 |
| 52 | 12 | 90 | 10 |
| 53 | 12 | 95 | 5 |
| 54 | 13 | 90 | 10 |
| 55 | 13 | 95 | 5 |
| 56 | 14 | 95 | 5 |
| 57 | 15 | 75 | 25 |
| 58 | 15 | 80 | 20 |
| 59 | 15 | 81.4 | 18.6 |
| 60 | 15 | 90 | 10 |
| 61 | 15 | 95 | 5 |
| 62 | 15 | 95.6 | 4.4 |
| 63 | 16 | 47.4 | 52.6 |
| 64 | 16 | 80 | 20 |
| 65 | 16 | 90 | 10 |
| 66 | 16 | 95 | 5 |
| 67 | 17 | 79.1 | 20.9 |
| 68 | 17 | 90 | 10 |
| 69 | 17 | 95 | 5 |
| 70 | 18 | 49.5 | 50.5 |
| 71 | 18 | 75 | 25 |
| 72 | 18 | 83 | 17 |
| 73 | 18 | 95 | 5 |
| 74 | 18 | 96.1 | 3.9 |
| 75 | 19 | 49.5 | 50.5 |
| 76 | 19 | 75 | 25 |
| 77 | 19 | 83 | 17 |
| 78 | 19 | 95 | 5 |
| 79 | 19 | 96.1 | 3.9 |
| 80 | 20 | 53.8 | 46.2 |
| 81 | 20 | 75 | 25 |
| 82 | 20 | 85.3 | 14.7 |
| 83 | 20 | 95 | 5 |
| 84 | 20 | 96.7 | 3.3 |
| 85 | 21 | 59.7 | 40.3 |
| 86 | 21 | 75 | 25 |
| 87 | 21 | 88.1 | 11.9 |
| 88 | 21 | 95 | 5 |
| 89 | 21 | 97.4 | 2.6 |
| 90 | 22 | 83.3 | 16.7 |
| 91 | 22 | 95 | 5 |
| 92 | 23 | 90 | 10 |
| 93 | 23 | 95 | 5 |
| 94 | 24 | 90 | 10 |
| 95 | 25 | 90 | 10 |
| 96 | 26 | 90 | 10 |
| 97 | 27 | 90 | 10 |
| 98 | 28 | 90 | 10 |
| 99 | 29 | 90 | 10 |
| 100 | 30 | 90 | 10 |
| 101 | 31 | 90 | 10 |
| 102 | 32 | 90 | 10 |
| 103 | 33 | 75 | 25 |
| 104 | 33 | 90 | 10 |
| 105 | 15 | 99.9 | 0.1 of Biocide A |
| 106 | 15 | 99.8 | 0.2 of Biocide a |
| 107 | 15 | 99.8 | 0.2 of Biocide B |
| 108 | 15 | 99.5 | 0.5 of biocide B |
| 109 | 15 | 99.9 | 0.1 of Biocide C |
| 110 | 15 | 99.8 | 0.2 of Biocide C |
| 111 | 15 | 99.9 | 0.1 of biocide D |
| 112 | 15 | 99.8 | 0.2 of Biocide D |

*For amphoteric co-polymer compositions see Table 1.
Biocide A n Butyl 1,2, benzisothiazolinone
Biocide B Dodecylethyldimethylammonium bromide
Biocide C 3-iodopropargylbutyl carbamate
Biocide D 2-octylisothiazolin-3-one Measurement of the Release Rate of Antimicrobial Agent (PHMB) from Films of Amphoteric Co-Polymer/PHMB Compositions by Calibration of poly(hexamethylene)biguanide (PHMB) Concentration By UV Spectrometry Firstly the UV absorbance at 236 nm of a known concentration of poly(hexamethylene biguanide) (PHMB) dissolved in water was measured (Perkin Elmer Lambda 900 UV/Vis/NIR Spectrometer). In a similar manner the UV absorbance at 236 nm was measured for a series of samples prepared from known dilutions of the original PHMB aqueous solution. A calibration curve for PHMB concentration in aqueous solution was produced (FIG. 3) by plotting UV absorbance against PHMB concentration.

Figure 3:
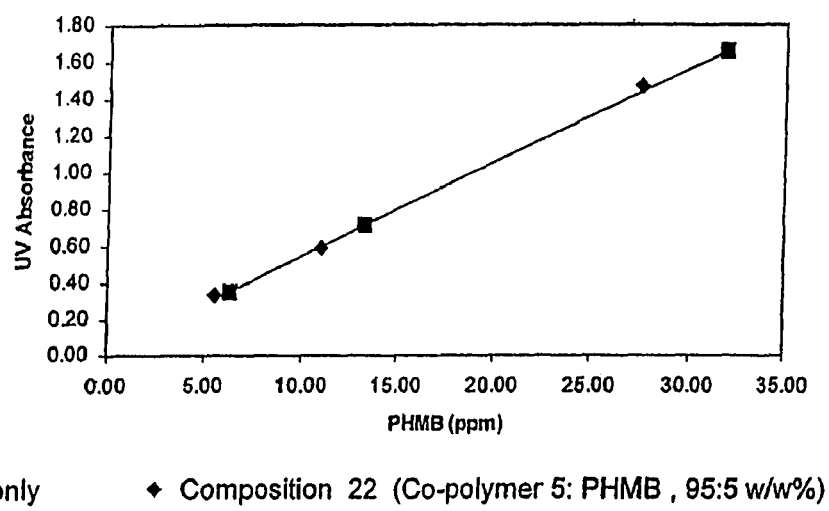
FIG. 3 shows a UV Spectroscopic Calibration Curve for Poly(hexamethylene biguanide) (PHMB) measured at 236 nm.

In addition, a similar UV calibration curve (FIG. 3) was produced for Composition 22) FIG. 3 illustrates that the presence of an amphoteric co-polymer does not significantly interfere with the determination of the PHMB concentration by this method.

Determination of the Release Rate Profiles of PHMB from Films of Co-Polymer/PHMB Compositions 1 to 104.

Amphoteric co-polymer/PHMB compositions were separately applied to clean glass panels (150 mm×100 mm) and films of the compositions were drawn down using a Sheen 250 μm draw down bar. The films were allowed to dry and the coating weight noted.

Each coated glass panel was immersed separately in distilled water (1L) in a 2L beaker and stirred at a constant speed using a magnetic stirrer.

Samples (approximately 5 cm$^3$) were taken from the beaker in duplicate at frequent time intervals.

The samples were analysed using a UV spectrophotometer and the absorbance of each sample measured at a specific peak corresponding to the λ max of poly(hexamethylene biguanide) (PHMB). The measured absorbance was directly related to the concentration of the PHMB in the beaker using calibration FIG. 3.

Using the methodology described above, the following release profiles (FIGS. 4-9) were generated.

Figure 4:
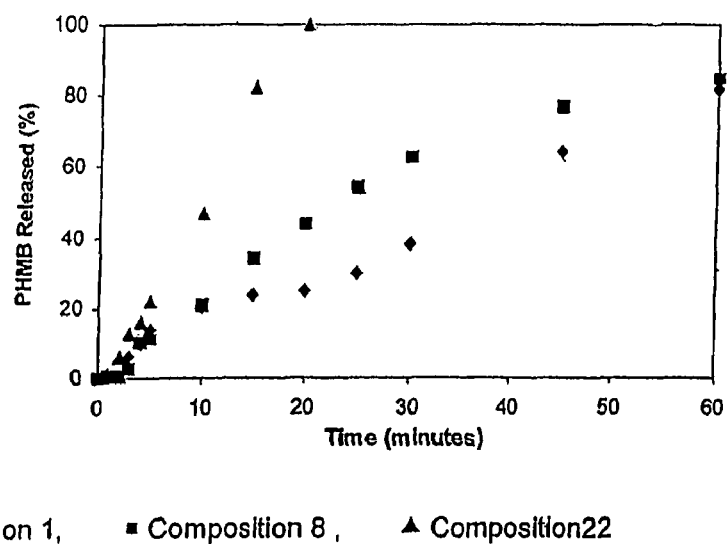
FIG. 4 shows a graph of the release of PHMB from coatings of Amphoteric co-polymer/PHMB compositions 1, 8 and 22.

From FIG. 4 the following conclusions can be drawn:
(i) Compositions 1, 8 and 22 each demonstrate controlled release of PHMB.
(ii) Composition 22 which contains Polymer 5 and has the highest PEG content of the 3 compositions releases PHMB at the highest rate.
(iii) Composition 1 which contains Polymer 1 and has the least PEG content of the 3 compositions releases PHMB at the slowest rate.
(iv) Composition 22 fully releases all PHMB after approximately 25 minutes.

(v) Compositions 1 and 8 release approximately 80% of the PHMB after 1 hour.
(iv) The release rate profile of PHMB from the amphoteric co-polymer/PHMB film can be controlled by the polymer architecture.

Figure 5:
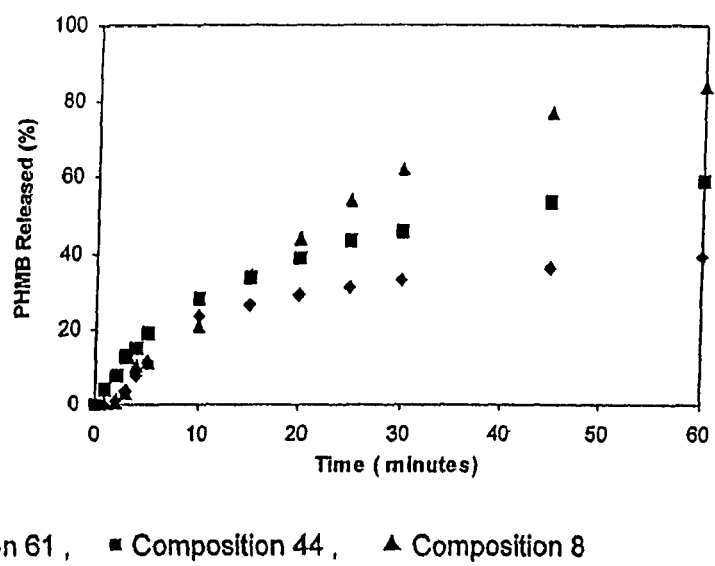
FIG. 5 shows a graph of the release of PHMB from coatings of Amphoteric co-polymer/PHMB compositions 8, 44 and 61 at 5% PHMB concentration.

From the FIG. 5 the following conclusions can be drawn:
(i) Compositions 8, 44 and 61 each demonstrate controlled release of PHMB.
(ii) Composition 8, which contains Polymer 2 and has the highest PEG content of the 3 compositions releases PHMB at the highest rate.
(iii) Composition 61, which contains Polymer 15 and has the least PEG content of the 3 compositions releases PHMB at the slowest rate.
(iv) Compositions 8, 44 and 61 release approximately 90, 60 and 40%, respectively, of the PHMB after 1 hour.
(v) As the polymer composition becomes more hydrophobic as a result of the introduction of more hydrophobic components [A], then the rate at which the polymer film releases PHMB decreases.
(vi) The release rate profile of the PHMB from the polymer film can be controlled by the polymer architecture.

Figure 6:
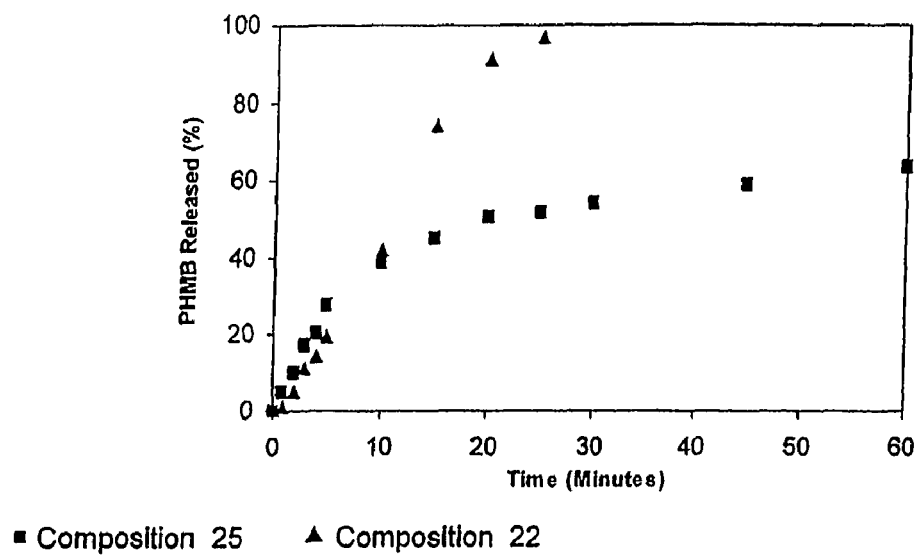
FIG. 6 shows a graph of the release of PHMB from coatings of Amphoteric co-polymer/PHMB compositions 22 and 25 at 5% PHMB concentration.
Figure 7:
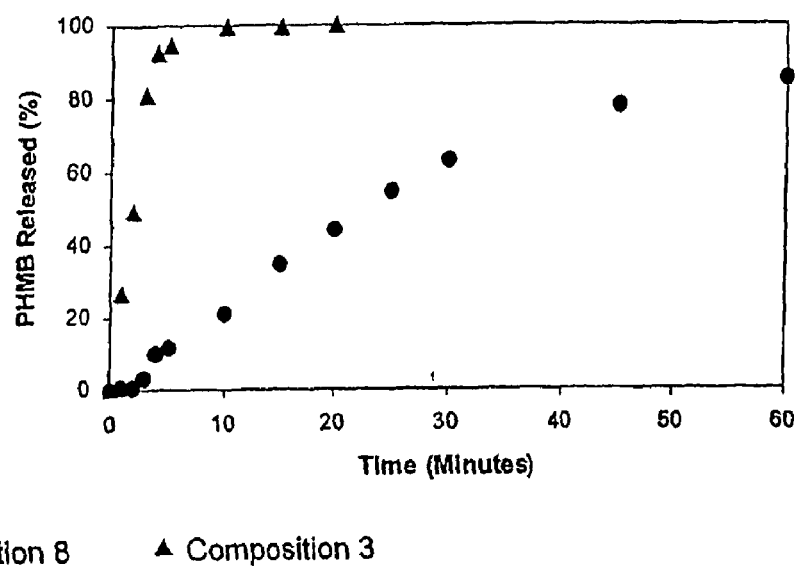
FIG. 7 shows a graph of the release of PHMB from coatings of Amphoteric co-polymer/PHMB compositions 8 and 3.

From the FIG. 6 the following conclusions can be drawn:
(i) Compositions 22 and 25 each demonstrate controlled release of PHMB.
(ii) Composition 22, which contains Polymer 5 and has the higher PEG content, releases PHMB at the highest rate.
(iii) Composition 25 releases approximately 60% of the PHMB present after 60 minutes compared to Composition 22, which released all its PHMB after approximately 25 minutes.
(iv) The release rate profile of the PHMB from the co-polymer/PHMB film can be controlled by the polymer architecture.

Compositions 8 and 3 are based on Polymer 2 but Composition 8 contains 5% by weight PHMB whereas Composition 3 contains 50% by weight PHMB. FIG. 6 shows that films of Composition 3 are not able to provide a sustained controlled release of PHMB, since all of the PHMB has been released from the film after less than 5 minutes. Therefore the loading of PHMB in the film is an important factor in determining the release rate profile.

Figure 8:
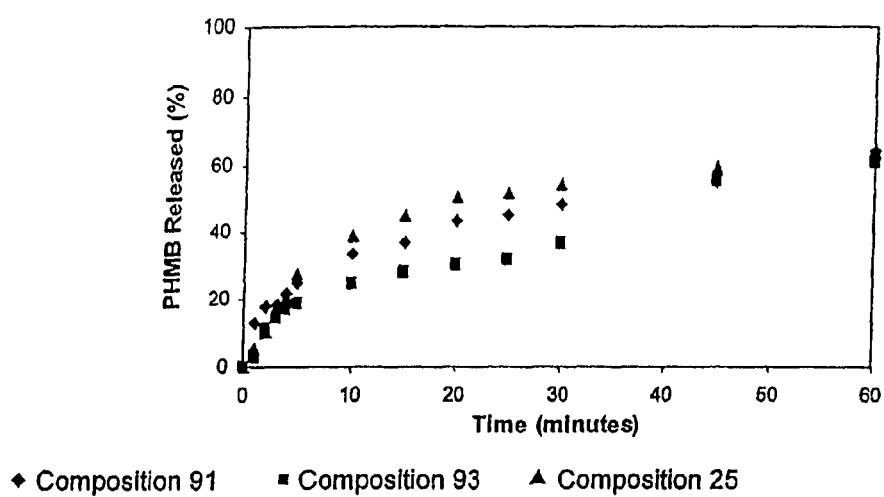
FIG. 8 shows a graph of the release of PHMB from coatings of Amphoteric co-polymer/PHMB compositions 25, 91 and 93.

From the FIG. 8 the following conclusions can be drawn:
(i) All three compositions provide a controlled release of PHMB after 1 hour.
(ii) All three formulations release approximately 60% of PHMB after 1 hour.
(iii) The more hydrophobic Composition 93 containing Polymer 23 has the slowest PHMB release rate over the first 30 minutes.

Figure 9:
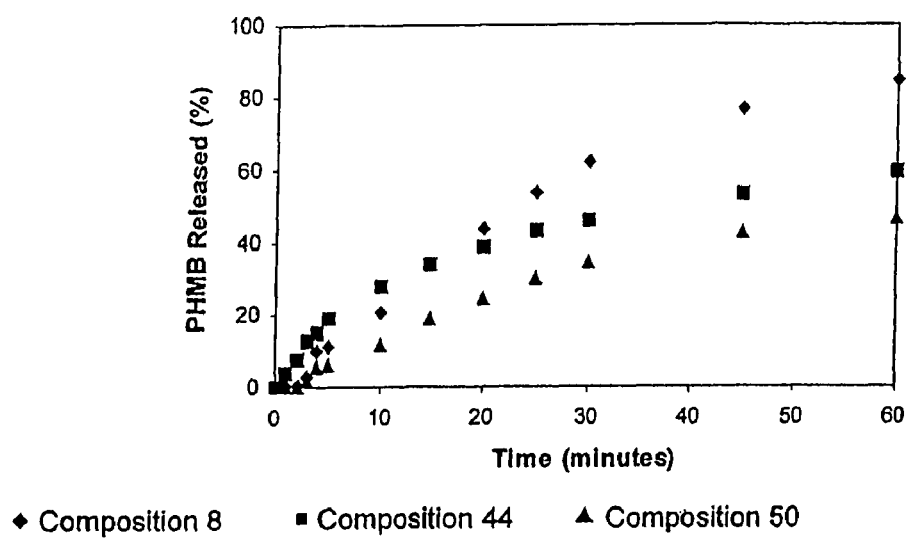
FIG. 9 shows a graph of the release of PHMB from coatings of Amphoteric co-polymer/PHMB compositions 8, 44 and 50.

From the FIG. 9 the following conclusions can be drawn:
(i) Compositions 8, 44 and 50 each demonstrate controlled release of PHMB.
(ii) Composition 8, which contains Polymer 2 and has the highest PEG content of the 3 compositions releases PHMB at the highest rate.
(iii) Composition 50, which contains Polymer 11 and has the least PEG content of the 3 compositions releases PHMB at the slowest rate.
(iv) Compositions 8, 44 and 50 release approximately 90, 60 and 45% of the PHMB respectively after 1 hour.
(v) As the polymer composition becomes more hydrophobic through the introduction of more MMA (monomer component [A]) then the rate at which the co-polymer/PHMB film releases PHMB decreases.

(vi) The release rate profile of PHMB from the co-polymer film can be controlled by the polymer architecture.

Therefore, according to the present invention it was found that the rate of dissolution of the polymeric biguanide (PHMB) from an amphoteric co-polymer could be controlled through the amphoteric polymer structure and the loading of the PHMB in the composition. Moreover, the above examples illustrate that stable amphoteric co-polymer solutions in both water and water/ethanol mixture, can be prepared with polymeric biguanides such as PHMB. PHMB is poly(hexamethylenebiguanide) hydrochloride available from Avecia Limited as Vantocil IB™.

Calculation of Minimum Inhibitory Concentrations.

The intrinsic antimicrobial activity of the polymer/PHMB compositions were evaluated by measuring Minimum Inhibitory Concentrations (MICs).
1. Bacteria (*Pseudomonas aeruginosa* ATCC 15442) were grown on nutrient agar for 16 to 24 hours at 37° C. (to give approximately $10^9$ cells per ml).
2. A 0.1% (v/v) inoculum was used to seed fresh medium and 100 μl was then added to each well of a microtitre plate, except for the first well which contained 200 μl.
3. Using doubling dilutions, the concentration of the compounds under investigation were varied in each well along the ordinate axis.
4. The presence or absence of growth was determined by visual inspection after 24 hours incubation at 37° C.

The MIC is the lowest concentration of the sample required to inhibit bacterial growth.

TABLE 3

Intrinsic Activity of Amphoteric Vinyl Co-polymer Compositions with PHMB.

| Composition Number (Table 2) | % by weight PHMB on Amphoteric Co-polymer | MIC versus *Pseudomonas aeruginosa* (ppm) |
|---|---|---|
| 2 | 60.6 | 31 |
| 5 | 22.9 | 31 |
| 7 | 5.8 | 31 |
| 9 | 66.3 | 24 |
| 10 | 56.4 | 24 |
| 11 | 28.2 | 16 |
| 13 | 7.3 | 31 |
| 15 | 55.6 | 24 |
| 16 | 20.6 | 31 |
| 18 | 4.9 | 16 |
| 20 | 20 | 31 |
| 23 | 4.8 | 62 |
| 26 | 51.5 | 31 |
| 28 | 17.5 | 31 |
| 30 | 4.1 | 8 |
| 31 | 69.4 | 31 |
| 32 | 31.3 | 31 |
| 33 | 8.4 | 188 |
| 35 | 62.9 | 31 |
| 36 | 25.2 | 31 |
| 38 | 6.3 | 62 |
| 40 | 54.4 | 16 |
| 42 | 19.3 | 16 |
| 45 | 4.6 | 31 |
| 46 | 49.6 | 31 |
| 48 | 16.4 | 31 |
| 51 | 3.8 | 93 |
| 75 | 50.5 | 31 |
| 77 | 17 | 31 |
| 79 | 3.9 | 31 |
| 80 | 46.2 | 31 |
| 82 | 14.7 | 31 |
| 84 | 3.3 | 46 |

TABLE 3-continued

Intrinsic Activity of Amphoteric Vinyl Co-polymer Compositions with PHMB.

| Composition Number (Table 2) | % by weight PHMB on Amphoteric Co-polymer | MIC versus *Pseudomonas aeruginosa* (ppm) |
|---|---|---|
| 85 | 40.3 | 31 |
| 87 | 11.9 | 31 |
| 89 | 2.6 | 31 |
| Vantocil IB Control | 0 | 31 |

Sustained Bactericidal Activity of Amphoteric Co-Polymers with PHMB

Experimental Determination of the Residual Bactericidal Activity of Amphoteric Co-Polymer/PHMB Formulations.

Amphoteric co-polymer/PHMB compositions were prepared as previously described (Table 2).

The residual antibacterial activity of the samples was determined by the following methodology:

1. All compositions were diluted to 0.5% active ingredient (PHMB). A 50 µl aliquot of each sample was placed in a ceramic tile well and allowed to dry for approximately 1 hour.
2. Bacteria (*Ps.aeruginosa* ATCC 15442) were grown in nutrient broth at 37° C. for 16-20 hours.
3. An inoculum of approximately $10^8$ organisms per ml was prepared in physiological saline (0.85% NaCl).
4. A 150 µl aliquot of bacterial inoculum was pipetted into the ceramic tile. well previously coated by the PHMB/polymer composition, and incubated at room temperature.
5. After 5 minutes contact time the inoculum was removed by pipette and the number of surviving, viable organisms enumerated (samples were serially diluted in CEN neutraliser by $10^2$, a 1 ml aliquot was added to 9 ml of impedance broth and the RABIT™ was used to enumerate bacterial cells).
6. The PHMB/polymer coated ceramic wells were then washed up to five times with 5 ml aliquots of sterile distilled water.
7. Following each washing step, the samples were re-inoculated with a 150 µl aliquot of bacterial inoculum.
8. As above the inoculum was removed after 5 minutes and the number of viable organisms enumerated by the method described above.

The RABIT™ (Rapid Automated Bacterial Impedance Technique) measures the change in conductance of a bacterial suspension over time. Actively growing bacteria break down uncharged or weakly charged molecules in a defined media to give end products that are highly charged. The resultant increase in conductance can be directly related to bacterial concentration by the use of a calibration curve. (Further background relating to this known technique can be found in: Technical Reference Paper-RAB-03, Don Whitley Scientific, 14 Otley Road, Shipley, West Yorkshire, UK, BD17 7SE).

Table 4 summarises the sustained bactericidal activity of the Amphoteric co-polymer/PHMB formulations obtained using the above technique.

TABLE 4

Sustained Bactericidal Activity of Amphoteric Co-polymers with PHMB.

| Composition Number[1] | % PHMB by weight on amphoteric co-polymer | Log reduction versus. *Ps. aeruginosa* after 5 minutes contact time | | |
|---|---|---|---|---|
| | | No washes | 1 wash | 2 washes |
| Control | 100 | 6.6 | 4.6 | 0.2 |
| 2 | 60.6 | 6.8 | 2 | 0.1 |
| 4 | 25 | 7.1 | nt | 1 |
| 5 | 22.9 | 6.8 | 2 | 0.1 |
| 7 | 5.8 | 5.4 | 5.4 | 4.4 |
| 8 | 5 | 3.8 | nt | 1.8 |
| 9 | 66.3 | 6 | 5.7 | 0 |
| 11 | 28.2 | 6.8 | 6.7 | 0.4 |
| 12 | 25 | 5.7 | nt | 0.5 |
| 13 | 7.3 | 6.8 | 6.8 | 6.2 |
| 15 | 55.6 | 6.8 | 4.5 | 0.1 |
| 16 | 20.6 | 6.8 | 3.2 | 0.7 |
| 17 | 5 | 6.1 | nt | 7.4 |
| 18 | 4.9 | 5.2 | 5.6 | 1.7 |
| 24 | 10 | 4.0 | 4.4 | 3.0 |
| 26 | 51.5 | 6.8 | 3.8 | 0.4 |
| 27 | 25 | 7 | 6 | 2 |
| 28 | 17.5 | 6.8 | 3 | 0.3 |
| 29 | 5 | 7 | nt | 4.4 |
| 30 | 4.1 | 6.8 | 6.8 | 7.1 |
| 35 | 62.9 | 6.8 | 2.5 | 0.1 |
| 36 | 25.2 | 7 | 4.1 | 0.1 |
| 37 | 25 | 7 | 5.7 | 3.9 |
| 38 | 6.3 | 4 | 4.3 | 3.0 |
| 40 | 54.4 | 6.8 | 3.3 | 0.4 |
| 41 | 25 | 7.1 | nt | 3 |
| 42 | 19.3 | 6.8 | 4.1 | 0.4 |
| 43 | 10 | 2.8 | 4.2 | 2.2 |
| 44 | 5 | 6.4 | nt | 5.8 |
| 45 | 4.6 | 5.4 | 6.8 | 4.3 |
| 46 | 49.6 | 6.8 | 3.1 | 0.3 |
| 47 | 25 | 7.1 | nt | 1.8 |
| 48 | 16.4 | 6.8 | 2.4 | 0.2 |
| 49 | 10 | 7.3 | 3.0 | 0.6 |
| 50 | 5 | 4.8 | nt | 5.9 |
| 51 | 3.8 | 1.5 | 6.2 | 4.4 |
| 52 | 10 | 7.3 | 3.8 | 0.9 |
| 54 | 10 | 6.3 | 3.8 | 1.3 |
| 57 | 25 | 7.1 | nt | 3.8 |
| 58 | 20 | 1.8 | 4.4 | 3.1 |
| 59 | 18.6 | 6.7 | 6.8 | 1.4 |
| 60 | 10 | 7.3 | 4.8 | 1.1 |
| 61 | 5 | 1.6 | nt | 5.4 |
| 62 | 4.4 | 7.1 | 7.1 | 3.2 |
| 63 | 52.6 | 7.1 | 6.3 | 5.8 |
| 64 | 20 | 1.7 | 4.2 | 2.6 |
| 65 | 10 | 5.4 | 3.2 | 1.4 |
| 67 | 20.9 | 6.7 | 6.8 | 1.7 |
| 68 | 10 | 5.4 | 3.2 | 1.4 |
| 69 | 5.0 | 7 | 5 | 2.3 |
| 70 | 50.5 | 6.8 | 1.8 | 0 |
| 71 | 25 | 7.1 | nt | 1 |
| 72 | 17.0 | 6.2 | 5.2 | 0.3 |
| 73 | 5 | 4.7 | nt | 7.4 |
| 74 | 3.9 | 1.7 | 6.8 | 6.7 |
| 75 | 50.5 | 6.8 | 2.3 | 0.9 |
| 76 | 25 | 7 | 5.6 | 2.5 |
| 77 | 17.0 | 6.8 | 1.9 | 1.9 |
| 78 | 5 | 6.4 | nt | 6.5 |
| 79 | 3.9 | 3.7 | 6.8 | 7.1 |
| 80 | 46.2 | 6.8 | 2.8 | 0.6 |
| 81 | 25 | 7.1 | 5.7 | 3.9 |
| 82 | 14.7 | 6.8 | 2 | 0.5 |
| 83 | 5 | 2.5 | nt | 2 |
| 84 | 3.3 | 2 | 6.3 | 5.9 |
| 85 | 40.3 | 6.8 | 2.1 | 0.4 |
| 86 | 25 | 7.1 | 6.7 | 6.5 |
| 87 | 11.9 | 5.6 | 4.2 | 0.2 |
| 88 | 5 | 7.1 | nt | 7.3 |
| 89 | 2.6 | 1.4 | 6.8 | 7.1 |
| 90 | 16.7 | 6.2 | 6.9 | 3.2 |

TABLE 4-continued

Sustained Bactericidal Activity of Amphoteric Co-polymers with PHMB.

| Composition Number[1] | % PHMB by weight on amphoteric co-polymer | Log reduction versus. *Ps. aeruginosa* after 5 minutes contact time | | |
|---|---|---|---|---|
| | | No washes | 1 wash | 2 washes |
| 93 | 10 | 6.2 | 2.8 | 0.5 |
| 94 | 10 | 7.2 | 4.6 | 0.8 |
| 95 | 10 | 7.2 | 7.2 | 0.6 |
| 96 | 10 | 7.2 | 5.9 | 1.1 |
| 97 | 10 | 7.2 | 7.2 | 0.6 |
| 98 | 10 | 7.2 | 5.9 | 1.1 |
| 99 | 10 | 1.8 | 2.7 | 1.0 |
| 100 | 10 | 4.5 | 6.8 | 2.1 |
| 101 | 10 | 7.3 | 4.8 | 1.1 |
| 102 | 10 | 6.7 | 3.4 | 1.0 |
| 103 | 25 | 4.5 | 3.9 | 1.4 |
| 104 | 10 | 3.7 | 3.4 | 2.0 | nt = not tested
[1]= see Table
[1]= see table 2 for composition of copolymer with PHMB From the above Table 4 the following conclusions can be drawn:
(i) In the absence of amphoteric co-polymer, PHMB has no useful biocidal activity after two wash cycles.
(ii) The highest sustained biocidal activities were generally observed for formulations with PHMB loadings of less than 10% by weight on amphoteric co-polymers.
(iv) In many formulations a greater than log 5 reduction after 2 washes was achieved, this compares with a log reduction of 0.2 for PHMB alone.

Sustained Fungicidal Activity of Amphoteric Co-Polymers with Various Biocides

Experimental Determination of the Residual Fungicidal Activity of Amphoteric Co-Polymer/Biocide Formulations.

Amphoteric co-polymer/Biocide compositions were prepared as previously described (Table 2).

The residual antifungal activity of the samples was determined by the following methodology:
1. Films of each composition were created on glass microscope slides using a '0' K-Bar and allowed to dry for no less than 24 hours.
2. Fungi (*Aspergillus niger* ATCC 16404) were grown on malt agar plates at 25° C. for approx. 7 days.
3. An inoculum of approximately $10^7$ spores per ml was prepared in physiological saline (0.85% NaCl).
4. A 150 µl aliquot of fungal inoculum was added to the surface of the compositions and incubated at room temperature for 24 hours.
5. The number of surviving, viable organisms were then enumerated (samples were washed into a neutralising medium, serially diluted in physiological saline and plated out onto malt agar).
6. Each composition was then washed ten times by spraying with sterile distilled water.
7. Each composition was then re-inoculated and after 24 hours the number of viable organisms enumerated by the method described above.

Table 5 summarises the sustained fungicidal activity of the Amphoteric co-polymer/Biocide formulations obtained using the above technique.

TABLE 5

Sustained Fungicidal Activity of Amphoteric Co-polymers (Example 15) with Various Biocides.

| Composition | | Weight Ratio (w/w) | log reduction vs. *A. niger* @ 24 h after no. of spray washes; | |
|---|---|---|---|---|
| Number | Biocide | Biocide:polymer | 0 | 10 |
| 106 | Biocide A | 499:1 | 0.7 | 0.4 |
| 108 | Biocide B | 199:1 | 2.5 | 0.2 |
| 110 | Biocide C | 499:1 | 3.4 | 3.3 |
| 112 | Biocide D | 499:1 | 3.4 | 3.3 |

It can be concluded that not only can stable formulations be prepared with the various biocides but that a sustained effect could be maintained using the spray washing protocol.

The results in Table 5 show that 2 formulations gave excellent sustained fungicidal activity While the invention has been described above with references to specific embodiments thereof, it is apparent that many change, modifications, and variations can be made without departing from the inventive concept herein. Accordingly, it is intended to embrace all such changes, modifications and variations that fall within the spirit and broad scope of the appended claims. All patent applications, patents and other publications cited herein are incorporated by reference in their entirety.

The invention claimed is:

1. A composition comprising:
(i) an anti-microbial agent comprising a linear polymeric biguanide, alone or in combination with at least one other microbiologically active component selected from the group consisting of quaternary ammonium compounds, monoquaternary heterocyclic amine salts, urea derivatives, amino compounds, imidazole derivatives, nitrile compounds, tin compounds or complexes, isothiazolin-3-ones, thiazole derivatives, nitro compounds, iodine compounds, aldehyde release agents, thiones, triazine derivatives, oxazolidine and derivatives thereof, furan and derivatives thereof, carboxylic acids and the salts and esters thereof, phenol and derivatives thereof, sulphone derivatives, imides, thioamides, 2-mercapto-pyridine-N-oxide, azole fungicides, strobilurins, amides, carbamates, pyridine derivatives, compounds with active halogen groups, and organometallic compounds; and
(ii) an amphoteric co-polymer of the Formula (1):

wherein:
[A] is of Formula (9),

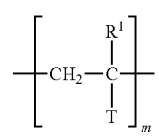

[B] is of Formula (10),

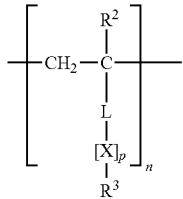
Formula (10)

[C] is of Formula (12),

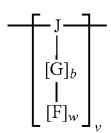
Formula (12)

[D] is of Formula (13),

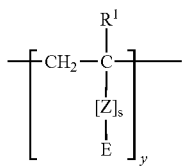
Formula (13)

and [X] is of Formula (11),

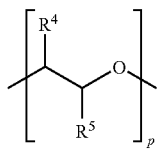
Formula (11)

wherein [A], [B], [C] and [D] may occur in any order;

T is an optionally substitutent selected from the group consisting of CN, OH, F, Cl, Br, —$OR^6$, —$C(O)R^6$, —$OC(O)R^6$, —$C(O)OR^6$, —$C(O)NR^7R^8$ and aryl, optionally substituted by —$OC(O)R^6$, F, Cl, Br, $C_{1-6}$-alkyl, —$CH_2Cl$ or —$C(O)OR^6$, wherein $R^6$ is a $C_{1-10}$-alkyl optionally substituted by a ketone, ether, epoxide, silane or ketoester group, and wherein $R^7$ and $R^8$ are each independently H, $C_{1-8}$-alkyl or $C_{3-8}$-cycloalkyl optionally substituted by —OH, ketone or alkyl ether groups;

L is an optionally substituted linking group represented by a formula selected from the group consisting of

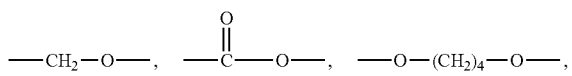

-continued

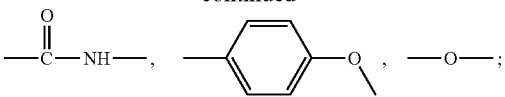

G is an optionally substituted linking group represented by a formula selected from the group consisting of

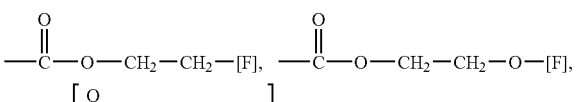

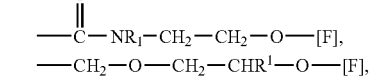

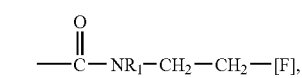

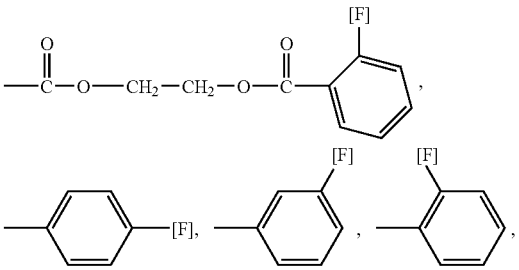

wherein d is selected from the group consisting of 2, 3, 4 and 5;

Z is an optionally substituted linking group represented by a formula selected from the group consisting of

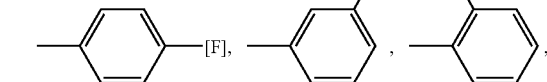

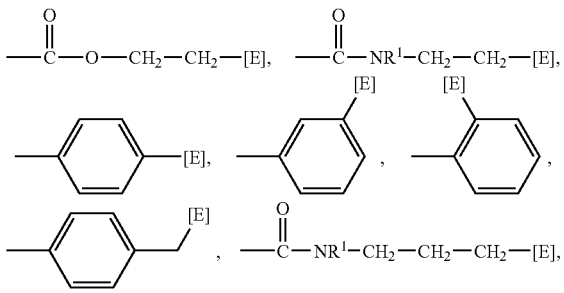

$R^1$, $R^2$ and $R^3$ are each independently H, optionally substituted $C_{1-20}$-alkyl or optionally substituted $C_{3-20}$-cycloalkyl;

$R^4$ and $R^5$ are each independently H or $C_{1-4}$-alkyl;

q is 15 to 1000;

p is 3 to 50;

J is an optionally substituted hydrocarbyl group;

F is an acidic substitutent;

E is a basic substitutent;

m is 0 to 350;

n is 1 to 75;

v is 1 to 100;

y is 1 to 100;

b is 0, 1 or 2;
s is 0 or 1;
w is 1 to 4; and
wherein [A] is present in the amphoteric co-polymer in an amount of from 0% to 45% by weight and [B] is present in said amphoteric co-polymer in an amount of from 5% to 95% by weight, said amounts being based on the total weight of the amphoteric co-polymer; and
provided that at least one of $R^4$ and $R^5$ is H.

2. The composition of claim 1 wherein the linear polymeric biguanide comprises a mixture of polymer chains in which the individual polymer claims excluding the terminating groups contain at least one recurring unit having two biguanide groups of Formula (4):

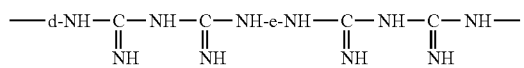

Formula (4)

wherein d and e represent bridging groups which may be the same or different and in which together the total of the number of carbon atoms directly interposed between the pairs of nitrogen atoms linked by d plus the number of carbon atoms directly interposed between the pairs of nitrogen atoms linked by e is more than 9 and less than 17.

3. A formulation comprising:
(i) a linear polymeric biguanide;
(ii) an amphoteric co-polymer; and
(iii) a carrier,
wherein the polymeric biguanide and amphoteric co-polymer are as defined in claim 1.

4. The formulation of claim 3 wherein the carrier is water or a mixture of water and/or a water miscible organic solvent.

5. The formulation of claim 3 which comprises from 0.01 to 5% by weight polymeric biguanide and from 0.01 to 50% by weight amphoteric co-polymer.

6. The formulation of claim 3 which comprises a pH in the range of from 1 to 12.

7. A method of substantially reducing and sustaining the level of micro-organisms on a surface which comprises contacting the surface with the composition of claim 1.

8. A method of substantially reducing and sustaining the level of micro-organisms on a surface which comprises contacting the surface with the formulation of claim 3.

* * * * *